United States Patent
Chiba et al.

(10) Patent No.: US 9,284,348 B2
(45) Date of Patent: *Mar. 15, 2016

(54) METHOD FOR SYNTHESIS OF PEPTIDE USING A CARRIER

(71) Applicant: JITSUBO Co., Ltd., Tokyo (JP)

(72) Inventors: Kazuhiro Chiba, Tokyo (JP); Shokaku Kim, Tokyo (JP); Yusuke Kono, Tokyo (JP)

(73) Assignee: JITSUBO Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/137,462

(22) Filed: Dec. 20, 2013

(65) Prior Publication Data

US 2014/0107319 A1 Apr. 17, 2014

Related U.S. Application Data

(62) Division of application No. 11/992,158, filed as application No. PCT/JP2006/318594 on Sep. 20, 2006, now Pat. No. 8,633,298.

(30) Foreign Application Priority Data

| Sep. 20, 2005 | (JP) | 2005-272905 |
| Feb. 1, 2006 | (JP) | 2006-024725 |
| Jul. 3, 2006 | (JP) | 2006-183688 |

(51) Int. Cl.

| C07C 229/08 | (2006.01) |
| C07C 271/22 | (2006.01) |
| C07C 227/40 | (2006.01) |
| C07C 227/42 | (2006.01) |
| C07C 269/06 | (2006.01) |
| C07C 269/08 | (2006.01) |
| C07C 43/23 | (2006.01) |
| C07C 51/09 | (2006.01) |
| C07B 63/00 | (2006.01) |
| C07B 63/02 | (2006.01) |
| C07K 1/00 | (2006.01) |
| C07K 1/30 | (2006.01) |
| B01D 9/00 | (2006.01) |
| C07C 41/16 | (2006.01) |
| C07C 51/44 | (2006.01) |
| C07C 67/60 | (2006.01) |
| C07C 227/18 | (2006.01) |
| C07K 1/04 | (2006.01) |
| C07K 5/083 | (2006.01) |
| C07C 39/10 | (2006.01) |

(52) U.S. Cl.
CPC ............... *C07K 1/306* (2013.01); *B01D 9/005* (2013.01); *C07B 63/00* (2013.01); *C07B 63/02* (2013.01); *C07C 39/10* (2013.01); *C07C 41/16* (2013.01); *C07C 43/23* (2013.01); *C07C 51/09* (2013.01); *C07C 51/44* (2013.01); *C07C 67/60* (2013.01); *C07C 227/18* (2013.01); *C07C 227/40* (2013.01); *C07C 227/42* (2013.01); *C07C 269/06* (2013.01); *C07C 269/08* (2013.01); *C07K 1/042* (2013.01); *C07K 5/0808* (2013.01)

(58) Field of Classification Search
CPC .. C07C 229/08; C07C 271/22; C07C 227/40; C07C 227/42; C07C 269/06; C07C 269/08; C07C 43/23; C07C 51/09; C07B 63/00; C07B 63/02; C07K 1/042; C07K 1/306; C07K 5/0808
USPC ......................................................... 530/344
See application file for complete search history.

(56) References Cited

U.S. PATENT DOCUMENTS

| 4,337,194 A | 6/1982 | Diaz et al. |
| 5,324,747 A | 6/1994 | Carson et al. |
| 5,712,367 A | 1/1998 | Bernard et al. |
| 8,344,103 B2 * | 1/2013 | Chiba et al. ................... 530/333 |

FOREIGN PATENT DOCUMENTS

| EP | 0421848 | 4/1991 |
| GB | 1464938 | 2/1977 |
| JP | 50-088003 | 7/1975 |
| JP | 55-162754 | 12/1980 |
| JP | 03-204894 | 9/1991 |
| JP | 2000-44493 | 2/2000 |

(Continued)

OTHER PUBLICATIONS

Hyunsoo Han et al., "Liquid-Phase Combinatorial Synthesis," Proc. Natl. Acad. Sci. USA, vol. 92, pp. 6419-6423, Jul. 1995 Chemistry.
Elliott JM, et al., "Crossover Phase Behavior (Discotic to Calamitic) in Liquid-Crystalline Copper Complexes.Dependence . . . Complexes", Inorg. Chem., vol. 40: pp. 6390-6396, 2001.
Wong JE, et al., "Optical and structural studies of Langmuir-Blodgett . . . of iridium(I)," Applied Surface Science, vol. 246: pp. 451-457, 2005.

(Continued)

*Primary Examiner* — Julie Ha
(74) *Attorney, Agent, or Firm* — Michael Ye; Andrews Kurth, LLP

(57) ABSTRACT

Disclosed are a carrier for use for separation purpose and a method for separation of a compound which enable a chemical reaction to be performed in a liquid phase, enable a compound of interest to be separated from the liquid phase after the completion of the reaction readily, enable the separated compound to be evaluated by structural analysis or the like while the compound being bound to the carrier, and enable the compound to be separated from the carrier readily. A carrier for separation which has a reaction site capable of reacting with other compound on a benzene ring, and a long-chain group having a specified carbon atom(s) at each of the ortho-position and the para-position of the reaction site through an oxygen atom.

5 Claims, 1 Drawing Sheet

(56) References Cited

FOREIGN PATENT DOCUMENTS

| JP | 2001-122889 | 5/2001 |
|---|---|---|
| JP | 2003-183298 | 7/2003 |
| JP | 2004-035521 | 2/2004 |
| JP | 2004-59509 | 2/2004 |
| JP | 2005-502748 | 1/2005 |
| JP | 2006-015283 | 1/2006 |
| WO | WO 03/022901 | 3/2003 |
| WO | WO 2005/087768 | 9/2005 |
| WO | WO 2006/104166 | 10/2006 |

OTHER PUBLICATIONS

Mamoru Mizuno at al. "Peptide synthesis on fluorous support", Tetrahedron letters, vol. 45, No. 17., pp. 3425-3428, 2004.

Philippe Berdague at al., "Influence de la substitution I aterale par des . . . complexes de cuivre", Bulletin de la Societe chimique de France, vol. 131, pp. 335-343, 1994.

The supplementary European search report issued to European Application No. 06798151.4, mailed Jul. 27, 2009.

Notice of Reasons for Rejection issued to JP Application No. 2007-536510, mailed Jun. 30, 2009.

* cited by examiner

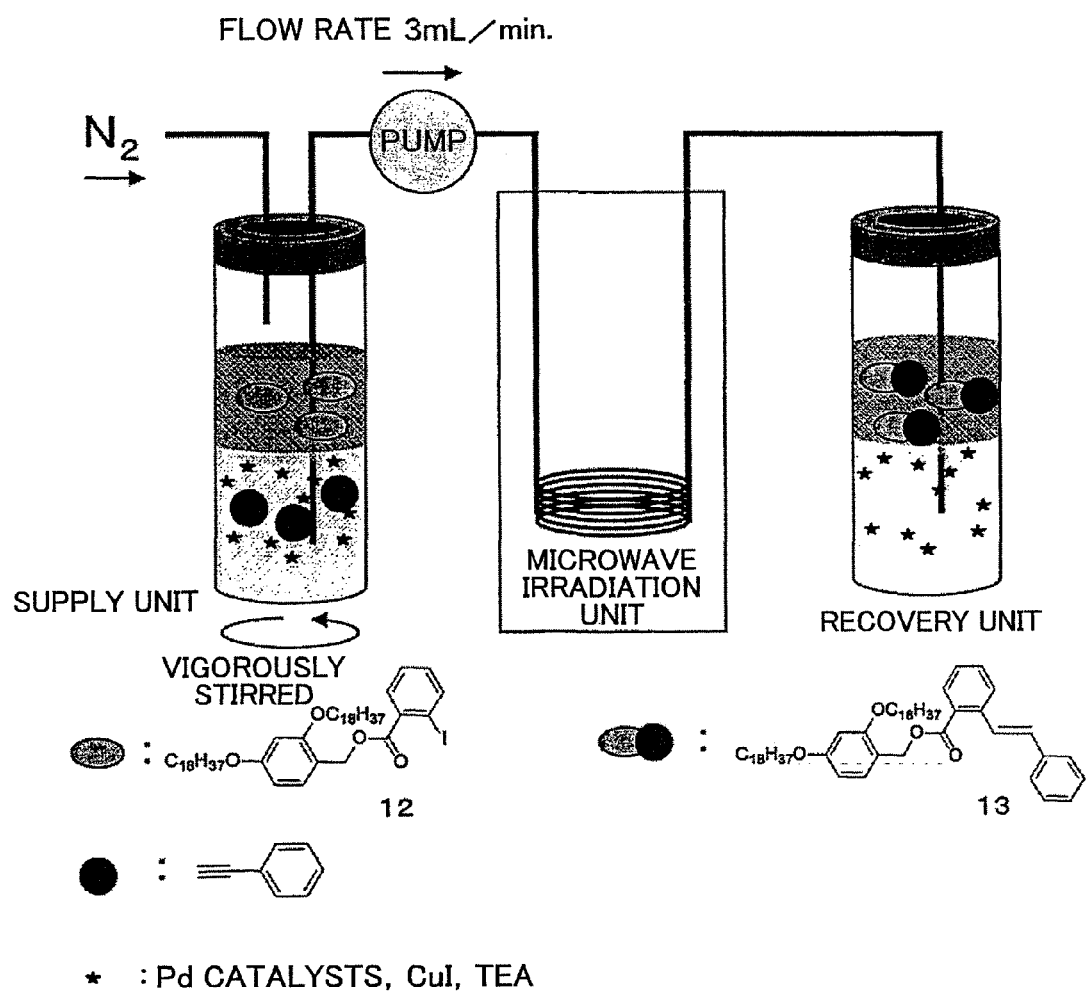

METHOD FOR SYNTHESIS OF PEPTIDE USING A CARRIER

This application is a divisional of U.S. Non-Provisional Patent Application No. 11/992,158 filed Oct. 13, 2009, which is a U.S. National Phase Patent Application under 35 U.S.C. §371 of International Patent Application No. PCT/JP2006/0318594, filed Sep. 20, 2006, entitled "CARRIER FOR SEPARATION, METHOD FOR SEPARATION OF COMPOUND, AND METHOD FOR SYNTHESIS OF PEPTIDE USING THE CARRIER," which claims priority to Japanese Patent Application No. 2005-272905 filed Sep. 20, 2005, Japanese Patent Application No. 2006-024725 filed Feb. 1, 2006 and Japanese Patent Application No. 2006-183688 filed Jul. 3, 2006, the contents of all are hereby incorporated in their entirety by reference.

TECHNICAL FIELD

The present invention relates to a carrier for separation and a method for separating a compound, more specifically a carrier for separation which has both a property to reversibly change from a liquid phase state to a solid phase state and crystallize according to changes in the composition and/or temperature of the solution, and a property to be selectively extracted in a specific phase and/or selectively crystallized in a specific phase according to changes in the composition and/or temperature of the solution, and a method for separating a compound using the carrier for separation.

BACKGROUND ART

Traditionally, in chemical processes, a method of separating a specific ingredient which has been dissolved in liquid as a solid has been widely used. This is because the solidification (crystallization) of only a specific ingredient enables separation and purification after the reaction to be performed readily. This method, for example, in sequential multi-step syntheses such as compound library synthesis or the like used in the recent development and research of drugs, etc. enables the solidified (crystallized) substance to be easily separated and purified by solidifying (crystallizing) a necessary or unnecessary compound after the completion of each reaction. Therefore, complications in the separation and/or purification process which have traditionally caused problems can be resolved.

Furthermore, a method of realizing the separation of a dissolved specific ingredient from other ingredients is also used by selectively dissolving the specific ingredient in a specific phase (selective partition) according to the phase separation of liquid. This method enables a specific ingredient to be separated without solidification (crystallization), thereby contributing to expediting and simplification of the process.

Such a solidification (crystallization) of a specific ingredient dissolved in solution or a selective dissolution of a specific ingredient in a specific phase of liquid (selective partition) can be realized by fulfilling certain conditions with respect to chemical and physical properties of the compound and the relationship with a solvent.

However, the conditions of solidification (crystallization) and selective dissolution (selective partition) must be empirically searched in most cases by trial and error. Especially, in sequential multi-step syntheses, it becomes necessary to examine the conditions of each step based on the specific property of a compound synthesized in each step, thereby having required tremendous amounts of money and time for the process development.

Therefore, there has been proposed a carrier molecule having a linker capable of sensitively perceiving the alteration of a solvent composition so as to reversibly change the soluble state and insoluble (crystallization) state, or selectively dissolving a specific dissolved ingredient into a specific phase in high concentration (selective partition) with the phase separation of the liquid. Such a carrier molecule can bind various compounds via the linker. Therefore, the bound compound can easily change states with the carrier molecule from a soluble state to an insoluble (crystallization) state or vice versa. Alternatively, the compound bound to the carrier molecule can be selectively dissolved in high concentration in a specific phase of liquid separated into multiphase (selective partition).

Furthermore, even when the chemical structure of a compound bound to such a carrier by the sequential multi-step reaction alters, the carrier molecule is capable of reversibly recreating the soluble state and insoluble (crystallized) state or dissolving in a specific phase of liquid separated into multiple phases selectively in high concentration (selective partition) under approximately the same conditions.

Using such a carrier molecule capable of reversibly changing the soluble state and insoluble (crystallized) state or inducing the selective partition state, it is possible to selectively separate an objective compound for separation from a homogeneous solution state while utilizing general knowledge of the liquid phase reaction in organic chemistry. That is, it has become possible to separate a specific compound after the liquid phase reaction while leaving other soluble ingredients in solution.

Concerning a carrier capable of reversibly repeating the soluble state and insoluble state, for example, a method of using a polymer soluble in solvents such as poly(ethylene glycol) is known (see Non-patent Document 1).

Non-patent Document 1: "Liquid-phase combinatorial synthesis" Hyunsoo Han, Mary M. Wolfe, Sydney Brenner, and Kim D. Janda, Proc. Natl. Acad. Sci. USA, Vol. 92, pp. 6419-6423, July 1995 Chemistry.

DISCLOSURE OF THE INVENTION

Problems to be Solved by the Invention

However, when a polymer such as poly(ethylene glycol) disclosed in Nonpatent Publication 1 is used as a carrier, it was difficult to evaluate a compound by structural analysis, etc. due to heterogeneity of the polymer while the compound is bound to the carrier. Furthermore, there were problems of complicated handling associated with difficulty in performing the anhydrous reaction because of the hydrophilicity of poly(ethylene glycol).

Besides the use of a carrier molecule capable of reversibly changing the soluble state and insoluble (crystallized) state or inducing the selective partition state, various solid phase extraction methods using solid carrier particles are known as the different separation method of compound. In the solid phase extraction method, for example, by specifically binding a ligand molecule having a high affinity to a probe molecule, which has been previously chemically bound to the surface of solid phase carriers such as silica gel, porous polymer, alumina and active carbon, the ligand molecule is separated differentially from other molecules. By this method, it is easy to perform a process of separating a substance captured by solid phase from a substance remaining dissolved in a liquid phase, and furthermore, it is possible to handle many samples in a short time and also to obtain reproducible good data without requiring expert skill, so that the method can be easily standardized by automated devices, etc.

However, in the solid phase extraction method using solid carrier particles, molecules other than the molecule specifically binding to ligand molecule may nonspecifically adsorb to the solid surface, causing the reduction of separation accuracy. Furthermore, in order to release the compound captured to the solid phase carrier surface again, it was required to perform specific treatments such as chemical treatment, biochemical treatment, light irradiation and application of electric stimuli. Therefore, even though it was easy to capture the objective compound from the liquid phase, a complicated process must have been further performed in the step of separating the objective compound from the solid phase.

The present invention has been performed in view of the above-described problems, and an objective of this invention is to provide a carrier for separation and a method for separation of a compound that enable a chemical reaction to be performed in a liquid phase, the specific compound to be separated from a liquid phase readily after the completion of the reaction, the separated compound to be evaluated by structural analysis or the like while the compound being bound to the carrier, and furthermore, the compound to be separated from the carrier readily.

Means for Solving the Problems

The present inventors have ardently performed research to solve the aforementioned problems. As a result, they have discovered that the abovementioned problems can be solved if a carrier for separation has a reaction site capable of binding to other compounds on a benzene ring, and a long-chain group having a specified number or more of carbon atoms at each of the ortho-position and the para-position of the reaction site through an oxygen atom, respectively, thereby achieving the present invention. More specifically, the present invention provides the following items.

According to a first aspect of the present invention, a carrier for separation is represented by the following formula (1) having a reaction site A capable of binding to another compound through any one of a carbon atom, oxygen atom, sulfur atom or nitrogen atom so as to separate the other compound.

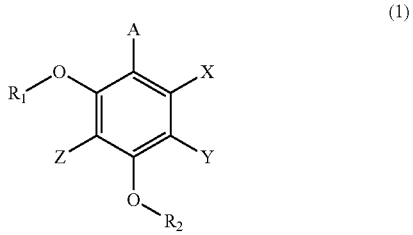

(1)

(in the formula,

A is a reaction site having one or more atoms selected from the group consisting of carbon, oxygen, sulfur and nitrogen atoms; in which X, Y and Z are each independently selected from any one of the group consisting of a hydrogen, a halogen, a hydrocarbon group having a carbon number in the range of 1 to 10 which may have a substituent, an acyl group having a carbon number in the range of 1 to 10 which may have a substituent, benzyl group and phenyl group; and $R_1$ and $R_2$ are groups, which may be identical or different, containing at least 1 of either a hydrocarbon group having a carbon number in the range of 14 to 60 which may be substituted or an acyl group having a carbon number in the range of 14 to 60 which may be substituted.)

The carrier for separation according to the first aspect enables a chemical reaction to be performed in a liquid phase, a specific compound contained in a liquid phase after the completion of the reaction to be reacted with and bound to the reaction site A, and other compounds to be selectively separated from a liquid phase. Thus, the objective compound can be efficiently separated in high purity.

Furthermore, since the carrier for separation according to the first aspect is not a polymer but a single compound, it enables the separated compound to be evaluated by structural analysis or the like, while the compound is bound to the carrier. Thus, the compound identification or the like can be performed without performing the separation process, so that it is possible to shorten the time required for compound identification and realize the promotion of research.

Furthermore, the carrier for separation according to the first aspect enables a compound reacted with and bound to the reaction site A to be separated from the carrier readily. Thus, the objective compound can be obtained efficiently in a shorter time compared with the case of performing traditional complicated processes such as chemical treatment, biochemical treatment, light irradiation and application of electric stimuli.

Furthermore, the carrier for separation according to the first aspect can reversibly recreate the soluble state and insoluble (crystallized) state or dissolve in a specific phase of liquid separated into multi-phase selectively in high concentration (selective partition) under approximately the same conditions, even when the chemical structure of other compounds bound to the reaction site A changes by the sequential chemical reactions. Therefore, it is unnecessary to investigate separation conditions based on specific characteristics, etc. of respective compounds.

Furthermore, the carrier for separation according to the first aspect includes at least of either a hydrocarbon group having a carbon number in the range of 14 to 60 or an acyl group having a carbon number in the range of 14 to 60 so as to contain a long-chain alkyl group. Thus, the carrier for separation according to the first aspect exhibits hydrophobicity and can dissolve into many organic solvents in high concentration. Therefore, the carrier for separation according to the first aspect can be widely applied without selecting the type of liquid into which the objective compound is dissolved.

The carbon number of the hydrocarbon group is preferably in the range of 14 to 50, more preferably in the range of 16 to 40, and most preferably in the range of 18 to 30. The carbon number of the acyl group is preferably in the range of 14 to 50; more preferably in the range of 16 to 40, and most preferably in the range of 18 to 30. As long as the carbon number is within the above-described range, sufficient hydrophobicity can be exhibited, and the range of choice of organic solvents is wide.

Furthermore, in the carrier for separation according to the first aspect, as shown in formula (1), X, Y and Z on the benzene ring are each independently selected from any one of the group consisting of a hydrogen, a halogen, a hydrocarbon group having a carbon number in the range of 1 to 10 which may have a substituent; an acyl group having a carbon number in the range of 1 to 10 which may have substituent; a benzyl group; and a phenyl group. Therefore, the carrier for separation according to the first aspect will be sufficiently effective as a carrier for separation even when it remains to have an unsubstituted hydrogen atom, but can be imparted with the required characteristics in accordance with the type of solvents and the type of compounds to be reacted with and bound thereto, and so on by introducing a halogen, a hydrocarbon having a carbon number in the range of 1 to 10 which may have substituent, an acyl group having a carbon number in the range of 1 to 10 which may have a substituent, a benzyl group, and phenyl group.

In the case of a hydrocarbon group which may have a substituent, the carbon number is preferably in the range of 1 to 8, and more preferably in the range of 1 to 6. Furthermore, in the case of an acyl group which may have a substituent, the carbon number is preferably in the range of 2 to 8, and more preferably in the range of 2 to 6. If the carbon number is within the above-described range, the carrier for separation of the first aspect can exhibit superior solubility toward many organic solvents.

Since the carrier for separation of the first aspect has various effects as described above, it not only enables the process to be developed readily, but also enables, for example, the research and development of drugs, etc. by the compound library synthesis or the like to be promoted, so as to be able to eventually contribute to technical innovation in the biochemical industry and chemical industry.

According to a second aspect of the carrier for separation according to first aspect of the present invention, the carrier for separation is capable of reversibly changing from a liquid phase state to a solid phase state, and crystallizing or solidifying while the carrier being bound with the other compound according to changes in the composition and/or temperature of the solution into which the carrier for separation dissolves or the liquid phase into which the carrier for separation melts.

The carrier for separation according to the second aspect includes one of a hydrocarbon group having a carbon number in the range of 14 to 60 and an acyl group having a carbon number in the range of 14 to 60, so as to contain a long-chain alkyl group. Since a long-chain alkyl group shows hydrophobicity, it enables the carrier for separation to dissolve in many solvents and at the same time enables the carrier for separation to crystallize readily by adding a solvent of high polarity.

Therefore, the carrier for separation according to the second aspect enables only the objective specific compound to be crystallized or solidified accompanied with the carrier, while ingredients other than the objective compound are left in a liquid phase by changing the composition and/or temperature of the solution into which the carrier dissolves or the liquid phase into which the carrier melts. The carrier for separation accompanied with another compound, either crystallized or solidified, can be easily separated from the liquid phase by filtration and so on, etc., so that a complex excision process can be avoided.

The carrier for separation according to the second aspect enables the objective compound to be evaluated by structural analysis or the like without separating the objective compound from the carrier while the compound is bound to the carrier. Therefore, evaluation of a compound by structural analysis or the like can be performed without going through the process of separating the compound from the carrier, so that in the research and development scene, the time required can be shortened so as to realize promotion thereof.

According to a third aspect of the carrier for separation according to the first aspect, the carrier for separation is selectively extracted and/or selectively crystallized in a specific phase according to changes in the composition and/or temperature of a solution into which the carrier for separation dissolves, while the carrier is bound to the other compound.

The carrier for separation according to the third aspect is a carrier which enables the carrier to be selectively extracted (as a liquid) and/or selectively crystallized in a specific phase of multiple phases after binding the objective compound to the carrier while the compound is bound thereto. Thus, only the objective specific compound can be separated while ingredients soluble in another liquid phase than that of the objective compound are left in the other liquid phase, so that the complex excision process can be avoided.

When the carrier for separation according to the third aspect is one selectively crystallized in a specific phase, it enables the structural analysis and so on, etc. to be performed as it is without separating the objective compound from the carrier so as to have the same effect as that of the above-described carrier of according to the second aspect.

In a fourth aspect of the carrier for separation according to the first aspect, the carrier for separation is capable of reversibly changing from a liquid phase state to a solid phase state according to changes in the composition and/or temperature of the solution in which the carrier for separation dissolves or the liquid phase in which the carrier for separation melts, and binding with the other compound in a solid phase state.

The carrier for separation according to the fourth aspect is one which reversibly changes from a liquid state to a solid state according to changes in the composition and/or temperature of solution before binding another compound, subsequently capturing the other compound by binding it to the carrier for separation which has transformed to the solid phase state so as to perform the so-called solid phase extraction.

Due to the solid state extraction, the carrier for separation according to the fourth aspect enables the process of separating the solid phase carrier which has captured a compound by binding thereto from the liquid phase to be readily performed, and subsequently enables the process for separating the compound from the carrier to be also simply carried out.

In a fifth aspect of the present invention, a method for separation of a compound includes a dissolution process of dissolving the carrier for separation according to the first aspect in a soluble solvent to prepare a carrier solution; a first binding process of binding another compound to the reaction site A of the carrier for separation; a crystallization process of crystallizing the carrier for separation while the other compound is bound to the carrier; or a selection process of selectively extracting and/or selectively crystallizing the carrier for separation into a specific phase while the other compound is bound to the carrier.

The method of separating a compound according to the fifth aspect is a separation method of performing crystallization or extraction after binding the objective compound to a carrier using the carrier for separation of the present invention. The method of separating a compound according to the fifth aspect includes both a case of solidifying (crystallizing) the carrier in a single liquid phase, while the compound is bound to the carrier, and a case of selectively extracting (as a liquid) and/or selectively crystallizing the carrier into a specific phase among multiple liquid phases while the compound is bound thereto.

The method of separating a compound according to the fifth aspect enables the specific compound to be selectively crystallized or extracted. Therefore, only the specific objective compound can be separated while ingredient(s) soluble in the liquid phase other than the objective compound is/are left in the liquid phase, thereby avoiding complex separation processes.

Furthermore, when the carrier is separated by crystallization by way of the separation method according to the fifth aspect while the carrier is accompanied with the objective compound, structural analysis, etc. can be performed as it is without separating the objective compound from the carrier. Therefore, confirmation, etc. of the obtained compound can be performed without passing through the process of separating the compound after crystallization, so that in the research and development scene, the time required can be shortened so as to realize the promotion of research.

Therefore, the method of separating compound according to the fifth aspect is able to become an innovative technique in the separation and purification of biochemical substances, the search for drug candidate substances, and the constitution of novel chemical synthetic reaction methods and peptide continuous synthesis method, etc.

In a sixth aspect of the present invention, a method of separating a compound including a melting process of liquidizing the carrier for separation according to the first aspect by heating above the melting point thereof; a reaction process of binding another compound to the reaction site A of the liquidized carrier for separation by reacting therewith; and a solidification process of solidifying the carrier for separation while the other compound is bound thereto.

The method of separating a compound according to the sixth aspect is a separation method of liquidizing the carrier for separation itself of the present invention without using any solvent, and solidifying the carrier after binding the objective compound to the liquidized carrier for separation.

The method of separating a compound according to the sixth aspect enables the specific compound to be selectively bound thereto and separated therefrom. Since, in the method of separating a compound according to the sixth aspect, the carrier for separation is in a solid phase (solidified), only the specific objective compound can be easily separated, thereby avoiding a complex separation process can be avoided. Furthermore, the method of separating a compound according to the sixth aspect enables the objective compound to be evaluated by structural analysis, etc. while the compound is bound to the carrier.

According to a seventh aspect, the method of separating a compound according to the sixth aspect further includes, after the solidification process, a washing process of washing the carrier for separation with a poor solvent in which the solubility of the solidified carrier for separation is low, while the other compound is bound thereto and/or an extraction process of selectively extracting the carrier for separation into a specific solvent while the other compound is bound thereto.

The method of separating a compound according to the seventh aspect is a method including a process of washing a complex compound in which the solidified carrier for separation of the present invention is bound to the objective specific compound with a poor solvent and/or a process of selectively extracting the complex compound into a specific solvent. By this method, the purity of the complex compound of the carrier for separation and the specific compound obtained in the subsequent process can be increased.

According to an eighth aspect, the method of separating a compound according to any one of the fifth to seventh aspects includes, after the first binding process or the reaction process, a second binding process of further binding another compound to the other compound which has been bound to the reaction site A of the carrier for separation.

The method of separating a compound according to the eighth aspect is one including a process of binding another compound bound to the other compound bound to the reaction site A of the carrier for separation. The carrier for separation of the present invention is capable of reversibly recreating the soluble state and insoluble (crystallized) state or dissolving in a specific phase of a liquid separated into multiple phases selectively in high concentration (selective partition) under substantially the same conditions, even when the chemical structure of the other bound compound changes by the sequential chemical reactions. Therefore, a plurality of other compounds can be chemically bound in sequence to the reaction site A of the carrier for separation of the present invention as a point of origin.

According to a ninth aspect, a method for separation of a compound includes a dissolution process of dissolving the carrier for separation according to the first aspect in a soluble solvent to prepare a carrier solution; a crystallization process of crystallizing the carrier for separation; and a capturing process of capturing the other compound by binding thereof to the reaction site A of the crystallized carrier for separation.

The method of separating a compound according to the ninth aspect is a separation method of capturing the objective compound by binding it to the carrier using the carrier for separation of the present invention first after crystallizing (solidifying) the carrier for separation. Therefore, the method for separating a compound according to the ninth aspect is mainly used in the case of solidifying (crystallizing) the carrier in a single liquid phase.

The method of separating a compound according to the ninth aspect enables the objective specific compound to be captured selectively in the solid phase. Therefore, only the objective specific compound can be separated while ingredients other than the objective compound soluble in the liquid phase is left in the liquid phase, thereby avoiding a complex excision process.

Furthermore, the method of separating a compound according to the ninth aspect enables structural analysis, etc. to be performed as it is without separating the objective compound from the carrier. Therefore, confirmation, etc. of the obtained compound can be performed without passing through the process of separating the compound, so that in the research and development scene, the time required can be shortened so as to realize promotion of research.

Therefore, the method of separating compound according to the ninth aspect is able to become an innovative technique in the separation and purification of biochemical substances, the search for drug candidate substances, and the constitution of novel chemical synthetic reaction methods and peptide continuous synthesis methods, etc.

According to a tenth aspect, the method of separating a compound according to any one from the fifth to ninth aspects further includes an excision process of separating other compound from the carrier for separation bound with the other compound after the crystallization process, the selection process, the solidification process the extraction process, or the capturing process.

The method of separating a compound according to the tenth aspect includes a process of separating the compound accompanied with the carrier for separation from the carrier. By separating the compound from the carrier, the objective compound prepared by synthesis, etc. can be obtained as a single compound. Furthermore, the carrier for separation can also be subsequently reutilized after separating the compound.

According to an eleventh aspect, the method of separating a compound according to any one from the fifth to ninth aspects further includes a process of eliminating impurities from a solution in which the carrier for separation dissolves or from a liquid phase into which the carrier for separation melts before the crystallization process, the selection process, the solidification process, the extraction process, or the capturing process.

The method of separating a compound according to the eleventh aspect is one including a process of eliminating impurities from a solution in which the objective specific compound dissolves before the carrier for separation of the present invention binds with the objective specific compound. Thereby, the purity of the complex compound of the carrier for separation and specific compound obtained in the subsequent process can be raised.

According to a twelfth aspect, in the method of separating a compound according to the fifth or any one from the eighth to eleventh, the selection process or the crystallization process is performed by a means of changing the composition of a solution in which the carrier for separation dissolves and/or a means of changing the temperature of a solution in which the carrier for separation dissolves.

The method of separating a compound according to the twelfth aspect is a method of crystallizing the carrier bound with the specific compound, extracting the carrier bound with the specific compound, or crystallizing (solidifying) the carrier itself by changing the composition and/or the temperature of a solution in which the carrier for separation dissolves.

The carrier for separation of the present invention sharply responds to changes in the composition and/or temperature of a solution in which the carrier for separation dissolves. Therefore, the carrier for separation accompanied with a compound can be crystallized or extracted, or the carrier itself can be crystallized (solidified) using a means of changing the composition and/or temperature of the solution. Furthermore, in this case, other soluble substances not bound to the carrier for separation can maintain the state left in solution.

According to a thirteenth aspect, in the method for separation of a compound according to the twelfth aspect, the means of changing the solution composition is a means of adding a solvent having a high affinity toward the soluble solvent.

The method of separating a compound according to the thirteenth aspect is a method of adding, to a solution in which the carrier for separation itself or the carrier for separation bound to the compound dissolves, a solvent having a high affinity toward the solution. The solution composition can be altered by adding a high affinity solvent, so that the carrier itself or the carrier for separation bound to the compound can be crystallized or extracted.

According to a fourteenth aspect, in the method for separation of a compound according to twelfth aspect, the means of changing the composition is a means of dividing the solution into multiple phases by adding a solvent having low affinity toward the soluble solvent.

The method of separating a compound according to the fourteenth aspect is a method of dividing a solution in which the carrier for separation itself or the carrier for separation bound to the compound dissolves into multiple phases by adding a solvent having a low affinity toward the solution. Thus, by adding a low affinity solvent, it is possible to change the solution composition and divide it into multiple phases, and at the same time transfer the carrier for separation itself or the carrier for separation bound to the compound selectively to a specific phase.

According to a fifteenth aspect, in the method for separation of a compound according to the twelfth aspect, the means of changing the composition is a means of concentrating the soluble solvent.

The method of separating, a compound according to the fifteenth aspect is a method of concentrating a solution in which the complex compound of the carrier for separation and specific compound dissolves. By concentrating the solution, the concentration of the complex compound of the carrier for separation and specific compound is elevated. Thus, it becomes possible to change the solution composition and crystallize the carrier for separation accompanied with the compound.

According to a sixteenth aspect, in the method of separating a compound according to the twelfth aspect, the means for changing temperature is a means of cooling the solution.

The method of separating a compound according to the sixteenth aspect is a method of realizing the temperature change by cooling the solution. By cooling the solution, it is possible to change the solution temperature and crystallize or extract the carrier for separation itself or the carrier for separation bound to the compound.

According to a seventeenth aspect, in the method of separating a compound according to any one from the sixth to eighth aspects or from the tenth to eleventh aspects, the solidification process is carried out by a means of adding a poor solvent in which the solubility of the carrier for separation is low to the carrier for separation bound to the other compound.

According to an eighteenth aspect, in the method of separating a compound according to any one from the seventh to eighth aspects or from the tenth to eleventh aspects, the extraction process is carried out by a means of adding a solvent capable of dissolving the carrier for separation bound with the other compound.

According to a nineteenth aspect, in the carrier for separation according to the first aspect, in which the other compound is an amino acid; the reaction site A is an atomic group capable of binding to an amino acid; $R_1$ and $R_2$, which may be identical or different, are groups containing a carbohydrate group having a carbon number in the range of 14 to 30 which may have a substituent; or an acyl group having a carbon number in the range of 14 to 30 which may have substituent.

According to a twentieth aspect, in the carrier for separation according to the nineteenth aspect, the reaction site A is an atomic group having a hydroxyl group, a thiol group, an amino group or a carboxyl group capable of binding with an amino acid.

According to a twenty-first aspect, a method of synthesizing oligopeptide includes a dissolution process of dissolving the carrier for separation according to the nineteenth or twentieth aspect in a soluble solvent to prepare a carrier solution; a binding process of obtaining the carrier for separation bound to oligopeptide by binding amino acid to the reaction site A of the carrier for separation followed by sequentially binding other amino acids to the amino acid which has been bound to the carrier for separation; a crystallization process of crystallizing the carrier for separation while the oligopeptide is bound thereto; or a selection process of selectively extracting and/or selectively crystallizing the carrier for separation into a specific phase while the oligopeptide being is bound thereto; and an excision process of excising the oligopeptide from the carrier for separation bound to the oligopeptide after the crystallization process and the selection process.

Since the oligopeptide synthesis method according to twenty-first aspect can perform the synthetic reaction in the liquid phase, the reaction efficiency and volumetric efficiency are extremely high, so that even oligopeptides, the synthesis of which by the solid phase reaction method is difficult, can be synthesized. Furthermore, the carrier for separation in the state bound to oligopeptide contained in the liquid phase after the completion of reaction can be efficiently separated in high purity. Furthermore, since a solid phase reagent can be used when the oligopeptide is excised from the carrier for separation bound to oligopeptide, it is easy to eliminate the solid phase reagent different from the case of excision with a soluble reagent.

Therefore, the oligopeptide synthesis method according to the twenty-first aspect enables various peptides to be easily and speedily synthesized, and provided. This oligopeptide can be used also as a material for synthesis of existing oligopeptides, enabling the number of processes of peptide synthesis to be reduced a greatly.

Herein, the carrier for separation used in the oligopeptide synthesis method of the twenty-first aspect has, as shown in formula (1), an atomic group having a hydroxyl group, a thiol group, an amino group or a carboxyl group as A to bind to an amino acid. Thus, this carrier for separation can sequentially bind a plurality of amino acids via the atomic group A so as to synthesize oligopeptide. Furthermore, since the bond between this atomic group A and the oligopeptide is relatively easily cleaved, a solid phase reagent can be used when the oligopeptide is excised from the carrier for separation.

This amino acid may be an amino acid having no protective group, or may be a protected amino acid having protective groups such as a Fmoc (9-fluorenylmethoxycarbonyl) group and Cbz (benzyloxycarbonyl) group. Therefore, synthesized oligopeptides include, besides unmodified oligopeptides, modified oligopeptides having the protective group of an amino acid side chain residue, amino protective group of terminal amino acid, and carboxyl protective group.

According to a twenty-second aspect, in the oligopeptide synthesis method according to the twenty-first aspect, in which the crystallization process or the selection process is performed by a means of changing the composition of a solution in which the carrier for separation dissolves and/or a means of changing the temperature of a solution in which the carrier for separation dissolves.

The oligopeptide synthesis method of the twenty-first aspect is a method of crystallizing or extracting the carrier for separation bound to the oligopeptide by changing the composition and/or temperature of a solution in which the carrier for separation dissolves.

According to a twenty-third aspect, in the oligopeptide synthesis method according to the twenty-first or twenty second aspect, the excision process is performed by adding a solid phase reagent to a solution in which the carrier for separation dissolves.

According a twenty-fourth aspect, in the oligopeptide synthesis method according to the twenty-third aspect, the solid phase reagent is a solid acid reagent.

The oligopeptide synthesis method according to the twenty-third aspect is a method of excising oligopeptide from the carrier for separation by adding a solid phase reagent such as a solid acid, solid base and solid reducing agent to a solution in which the carrier for separation dissolves; and the oligopeptide synthesis method according to the twenty-fourth aspect is a method especially using a solid acid reagent as a solid phase reagent. The excised oligopeptide and solid phase reagent used in excision can be easily separated by filtration.

Effects of the Invention

The carrier for separation of the present invention enables a chemical reaction to be performed in a liquid phase, a specific compound contained in a liquid phase after the completion of the reaction to be reacted with and bound to the reaction site A, and other compounds to be selectively separated from the liquid phase. Therefore, the objective compound can be efficiently separated in high purity.

Furthermore, the carrier for separation of the present invention is not a polymer, but a single compound so that it enables the separated compound to be evaluated readily by structural analysis or the like while the compound is bound to the carrier. Therefore, confirmation of a compound, etc. can be performed without going through a separation process, so that the carrier for separation of the present invention can shorten the time required for chemical synthesis and realize promotion of research in the research and development scene.

Furthermore, the carrier for separation of the present invention enables the compound which is reacted with and bound to the reaction site A to be easily separated from the carrier. Thus, the objective compound can be obtained efficiently in a shorter time compared with the case of performing conventional complicated processes such as chemical treatment, biochemical treatment, light irradiation and the application of electric stimuli.

Furthermore, the carrier for separation of the present invention is capable of reversibly recreating the soluble state and insoluble (crystallized) state, or dissolving in a specific phase of liquid separated into multiple phases selectively in high concentration (selective partition) under substantially the same conditions, even when the chemical structure of other compound bound to the carrier changes by sequential chemical reactions. Therefore, it is unnecessary to investigate separation conditions based on specific characteristics, etc. of respective compounds.

Furthermore, the carrier for separation of the present invention shows superior solubility toward many organic solvents, so that it can be widely used without selecting the type of liquid in which the objective compound dissolves.

Therefore, since the carrier for separation of the present invention has the above-described effects, it is unnecessary to examine crystallization conditions or partition conditions based on specific properties, etc. of respective compounds. Thus, the carrier for separation of the present invention not only enables the process development to be made readily, but also enables, for example, the research and development of drugs, etc. by compound library synthesis or the like to be promoted, so as to be able to eventually contribute to the technical innovation in the biochemical industry and chemical industry.

Furthermore, the method for separation of a compound according to the present invention enables a specific compound to be selectively separated. That is, it enables only the specific objective compound to be separated while ingredient(s) soluble in a liquid phase are left therein, so as to be able to avoid a complicated excision process.

Furthermore, the method for separation of a compound according to the present invention can be widely applied without selecting the type of organic solvents since the carrier to be used shows superior solubility toward many organic solvents.

Therefore, the method for compound separation of the present invention can become an innovative technique in the separation and purification of biochemical substances, search for drug candidate substances, and constitution of a novel chemical synthetic reaction method and peptide continuous synthesis method, etc.

Furthermore, the present invention can synthesize various oligopeptides simply and quickly using a carrier for separation of the structure having one atomic group serving as the reaction site to bind to an amino acid on the benzene ring and one each of long chain groups having more than a specified number of carbon atoms at each of the ortho-position and the para-position of the atom group through an oxygen atom, respectively.

BRIEF DESCRIPTION OF THE DRAWINGS

FIG. 1 is a process chart showing the separation method using a carrier for separation.

PREFERRED MODE FOR CARRYING OUT THE INVENTION

Hereinafter, preferred embodiments of the present invention are described in detail.

Carrier for Separation

The carrier for separation of the present invention represented by the following formula (1) has a reaction site A to bind with other compound, and this reaction site A binds to the other compound through any one of a carbon atom, oxygen atom, sulfur atom or nitrogen atom so as to separate the other compound.

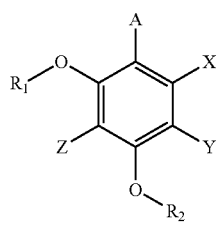

(1)

(in the formula,

A is a reaction site having more than 1 atom selected from the group consisting of carbon, oxygen, sulfur and nitrogen atoms;

X, Y and Z are each independently selected from any one of the group consisting of a hydrogen, a halogen, hydrocarbon group having a carbon number in the range of 1 to 10 which may have substituent, an acyl group having a carbon number in the range of 1 to 10 which may have a substituent, a benzyl group, and a phenyl group;

$R_1$ and $R_2$, which may be identical or different, are groups containing more than 1 of either a hydrocarbon group having a carbon number in the range of 14 to 60 which may be substituted or an acyl group having a carbon number in the range of 14 to 60 which may be substituted.)

Reaction site A

The reaction site A to bind to other compound on the carrier for separation of the present invention includes at least one atom selected from the group consisting of a carbon atom, oxygen atom, sulfur atom and nitrogen atom, and may contain a plurality of the same atom.

The size of the reaction site A is not particularly limited, and may be sufficient as long as the reaction site A, in its part, has a portion serving as a reaction site capable of binding to other compound. Furthermore, although the position in which the reaction site to bind to other compound is present in the reaction site A is not particularly limited, it is preferably present at the terminal end of the reaction site A to make the reaction proceed readily.

The reaction site A binds to other compound through any one selected from the group consisting of a carbon atom, nitrogen atom, sulfur atom and nitrogen atom. Although, in the reaction site A, the structure of the reaction site having any one selected from the group consisting of a carbon atom, nitrogen atom, sulfur atom and nitrogen atom to bind to other compound is not particularly limited, for example, a hydroxyl group, amino group, carboxyl group, thiol group, etc. can be exemplified.

The carrier for separation of the present invention may be one having an atomic group A serving as a reaction site to bind to an amino acid. The atomic group A is not particularly limited.

The carrier for separation of the present invention may be one having a hydroxyl group, thiol group, amino group or carboxyl group to bind to the amino acid so as to have an atomic group A serving as a reaction site to bind to the amino acid.

If this is the case, the size of the atomic group A is not particularly limited and may be sufficient as long as a part of the atomic group A has a hydroxyl group, thiol group, amino group or carboxyl group. Furthermore, the position in which the hydroxyl group, thiol group, amino group or carboxyl group is present in the atomic group A is not particularly limited, but it is preferably present at the terminal of the atomic group A for making the reaction proceed readily.

Furthermore, the number of reaction sites A in the carrier for separation of the present invention is only one on the benzene ring. Since the carrier for separation of the present invention has only one reaction site A, when separating a compound having one reactive part capable of binding to the reaction site A, the reaction ratio of the carrier for separation to the compound becomes 1:1. Therefore, in this case, subsequent structure analysis or the like becomes easy.

The carrier for separation of the present invention is of a structure having long-chain groups $R_1$ and $R_2$ of more than a specified number of carbon atoms at each of the ortho position and the para position of the reaction site A through an oxygen atom, respectively.

Herein, $R_1$ and $R_2$, which may be the same or different, are groups containing more than 1 of either a hydrocarbon group having a carbon number in the range of 14 to 60 or an acyl group having a carbon number in the range of 14 to 60. The carbon number of the hydrocarbon group is preferably in the range of 14 to 50, more preferably in the range of 16 to 40, and most preferably in the range of 18 to 30. The carbon number of the acyl group is preferably in the range of 14 to 50, more preferably in the range of 16 to 40, and most preferably in the range of 18 to 30. Specifically, alkyl groups such as octadecyl, icosyl and docosyl groups having a carbon number in the range of 18 to 22, and acyl groups such as stearoyl, icosanoyl and docosanoyl groups having a carbon number in the range of 18 to 22 can be exemplified.

Furthermore, when the atomic group A has a reactive site to bind with the amino acid, $R_1$ and $R_2$, which may be the same or different, are groups containing more than 1 of either hydrocarbon group having a carbon number in the range of 14 to 30 or an acyl group having a carbon number in the range of 14 to 30. The carbon number of the hydrocarbon group is more preferably in the range of 18 to 22. The carbon number of the acyl group is more preferably in the range of 18 to 22. Specifically, alkyl groups such as octadecyl, icosyl and docosyl groups having a carbon number in the range of 18 to 22, and acyl groups such as stearoyl, icosanoyl and docosanoyl groups having a carbon number in the range of 18 to 22 can be exemplified.

The carrier for separation of the present invention is carrier in which X, Y and Z on the benzene ring are respectively any one independently selected from the group consisting of a hydrogen, a halogen, hydrocarbons, which may have a substituent, having carbon number in the range of 1 to 10, acyl groups, which may have a substituent, having a carbon number in the range of 1 to 10, a benzyl group and a phenyl group. In the case of hydrocarbon groups which may have a substituent, the carbon number of which is preferably in the range of 1 to 8, more preferably in the range of 1 to 6. In the case of acyl groups, which may have a substituent, the carbon number of which is preferably in the range of 2 to 8, and more preferably in the range of 2 to 6.

The method of preparing the carrier for separation of the present invention is not particularly limited. For example, a method is cited in which after a 2,4-dihydroxybenzaldehyde derivative and alkyl bromide are heated in the presence of basic catalysts such as potassium carbonate to obtain an alkyletherified benzaldhyde derivative, the aldehyde is dissolved in a suitable solvent and reduced using reducing agents such as sodium bicarbonate to benzyl alcohol so as to obtain the carrier for separation.

Property of the Carrier for Separation

The carrier for separation of the present invention has properties to reversibly change from a liquid phase state to a solid phase state according to changes in the composition and/or temperature of a solution in which the carrier is dissolved or a liquid phase in which the carrier melts so as to crystallize or solidify while the carrier is bound to other compound.

Furthermore, the carrier for separation of the present invention also has properties to be selectively extracted and/or selectively crystallized in a specific phase according to changes in the composition and/or temperature of a solution in which the carrier is dissolved while the carrier is bound to other compound. Thus, it can be selectively extracted and/or crystallized in a specific phase of liquid phases divided into more than two phase.

Furthermore, the carrier for separation of the present invention is a carrier capable of reversibly changing from a liquid phase to a solid phase according to changes in the composition and/or temperature of a solution in which the carrier is dissolved or a liquid phase in which the carrier melts so as to also have properties to bind to other compound after becoming a solid phase state.

Method of Separating Compound

Methods of separating a compound of the present invention include the following three methods: (1) a method of performing crystallization and/or extraction after dissolving the carrier for separation of the present invention in a soluble solvent, and binding the objective specific compound to the carrier for separation; (2) a method in which, after melting the carrier for separation of the present invention itself to a liquid phase and binding the objective specific compound to the carrier in a liquid phase, the carrier for separation bound to the compound is solidified; and (3) a method in which, after dissolving the carrier for separation of the present invention in a soluble solvent and subsequently crystallizing (solidifying) it, the objective specific compound is captured by binding to the crystallized carrier. Hereinafter, each method is separately explained.

(1) (i) Method of Performing Crystallization and/or Extraction After Dissolving the Carrier for Separation of the Present Invention in a Soluble Solvent and Binding the Objective Specific Compound to the Carrier for Separation The method of separating a compound, in which the carrier for separation of the present invention is dissolved in a soluble solvent and first the objective compound is bound to the carrier for separation, includes: a dissolving process of dissolving the carrier for separation of the present invention in a soluble solvent to prepare a carrier solution; a first binding process of binding other compound to the reaction site A of the carrier for separation; a crystallization process of crystallizing the carrier bound to the other compound or a selection process of selectively extracting and/or selectively crystallizing the carrier for separation in a specific phase while the other compound being bound thereto.

Dissolution Process

The dissolution process of the present separation method is a process of dissolving the carrier for separation of the present invention in a soluble solvent to prepare a carrier solution. Soluble solvents used in the dissolution process are not particularly limited as long as they are capable of dissolving the carrier for separation of the present invention. For example, a halogenated hydrocarbon, linear ether, cyclic ether, cyclic or linear hydrocarbon having a number of carbon atoms in the range of 4 to 40 can be exemplified. More specifically, for example, dichloromethane, tetrahydrofuran, cyclohexane, methylcyclohexane, decalin, etc. can be exemplified. These solvents may be used by mixing one or more than 2 types thereof.

Although the concentration of the carrier for separation of the present invention when dissolving it in a soluble solvent can be appropriately selected according to the properties of the solvent to be used, a carrier for separation and a compound to be bound to the crystallized carrier for separation, it is usually in the range of 0.01 to 0.5 g/ml.

First Binding Process

The binding process in the present separation method is a process of obtaining a complex compound of the carrier for separation and other compound by binding the other compound to the reaction site A of the carrier for separation. Binding methods in the binding process are not particularly limited so far as they are methods of binding the other compound having a portion capable of reacting with the reaction site A to the reaction site A of the carrier for separation dissolved in a soluble solvent in the previous process, so that various chemical reactions in liquid phase can be used. For example, methods of binding by forming the ester bond and amide bond can be exemplified.

Second Binding Process

The present separation method may be a method including, after the above-described first binding process, a second binding process to further bind another compound to the other compound which has been bound to the reaction site A of the carrier for separation. In the present separation method, it is possible to bind a plurality of other compounds sequentially by chemical reactions to the reaction site A as a point of origin.

Compounds used when performing the sequential chemical reactions are not particularly limited so far as they are compounds capable of reacting with and binding to the compound which has been already bound to the reaction site A of the carrier for separation as a point of origin. Furthermore, the sequential chemical reactions may be performed in the same liquid phase containing the carrier for separation which has already become a complex compound with other compounds or in a different liquid phase after once solidifying (crystallizing) to separate the carrier for separation which has become a complex compound.

Impurity Eliminating Process

In the present separation method, it is preferable to include an impurity elimination process for eliminating impurities before performing the following crystallization process or selection process. In the following crystallization process or selection process, impurities contained in solution may be sometimes crystallized or extracted together with the carrier. Especially, when a means of distilling off all solvents is used as a crystallization process, impurities are precipitated together with crystals of the carrier for separation bound to the compound as the crystallization objective. Therefore, by previously eliminating impurities before performing the crystallization process or selection process, it is possible to raise the purity of the subsequently obtained crystals of the carrier for separation bound with the compound as the separation objective.

Although methods of eliminating impurities are not particularly limited, for example, a method of washing a whole solution in which a complex compound of the compound as a separation objective and the carrier for separation is dissolved with a solvent can be exemplified.

Crystallization Process

The crystallization process in the present separation method is a process of crystallizing a compound bound to the carrier for separation in a first binding process, a previous process, or further in a second binding process while the compound is accompanied with the carrier for separation. Although the crystallization process of the present separation method is not particularly limited, so far as it enables the crystallization of the compound as a separation objective while the compound is bound to the carrier for separation, for example, a means of changing the solution composition and/or the solution temperature can be preferably used.

Selection Process

The selection process of the present separation method is a process of selectively extracting (as a liquid) or selectively crystallizing a compound bound to the carrier for separation in a first binding process, a previous process, or further in a second binding process in a specific liquid phase while the compound is accompanied with the carrier. That is, in the separation method including the selection process, the liquid phase is in a state of multi-phase including more than two phases, so that the carrier for separation accompanied by a compound is selectively extracted (as a liquid) and/or crystallized in a specific liquid phase of multiple phases.

Although the selection process in the present separation method is not particularly limited, so far as the selection process enables a specific compound, which becomes a separation objective, to be extracted and/or crystallized while the compound is bound to the carrier for separation, for example, a means of changing the solution composition and/or a means of changing the solution temperature can be preferably used.

Means of Changing Composition

A means of changing the solution composition preferably used in the crystallization process or selection process of the present separation method is not particularly limited so far as it enables the composition of the solution in which a complex of the compound as a separation objective and the carrier for separation is dissolved to be altered.

In the present separation method, as a preferable means of changing the solution composition, for example, a means of further adding a solvent having a high affinity toward the soluble solvent used to dissolve the carrier for separation in the dissolution process is exemplified. When adding a solvent having a high affinity toward the soluble solvent, a liquid phase is maintained as a single phase without causing phase separation.

A high-affinity solvent may be the same as or different from the solvent used as a soluble solvent. For example, when dichloromethane, tetrahydrofuran, etc. is used as the soluble solvent, acetonitrile, dimethylformamide, methanol, etc. can be used.

In the present separation method, as another preferable means of changing the solution composition, for example, a means of further adding a solvent having a low affinity toward the soluble solvent used to dissolve the carrier for separation in the dissolution process can be exemplified. When adding a solvent having low affinity toward the soluble solvent, the liquid causes phase separation into a double phase. Thereby, the carrier for separation itself or the carrier for separation bound with a compound is transferred selectively to a specific phase.

For example, by dissolving the carrier for separation in cyclohexane, dissolving other compound and the other arbitrary reaction reagent or the like in dimethylformamide, and mixing the two solutions, and subsequently, after passing through a first binding process or furthermore a second binding process, by adding a small amount of an aqueous solution of propylene carbonate and ammonium salt corresponding to a low affinity solvent, the carrier for separation bound with the other compound can be selectively dissolved in the cyclohexane phase.

Furthermore, as yet another preferable means of changing the solution composition, for example, a means of concentrating the solvent of a solution, in which the complex compound of the compound as a separation objective and the carrier for separation is dissolved, is exemplified. Herein, concentration refers to partial or complete distillation of the solvent. In addition, when the carrier for separation bound with a compound is crystallized by the complete distillation of the solvent, impurities and so on contained in the solution may be crystallized together, so that it is preferable to include a process of eliminating impurities before performing the crystallization process.

Means of Changing Temperature

A means of changing solution temperature preferably used in the crystallization process or selection process of the present separation method is not particularly limited so far as they are means capable of changing the temperature of the solution in which the complex compound of the compound to be the separation objective and the carrier for separation is dissolved. In the present separation method, for example, a means of cooling the solution can be exemplified. For example, when cyclohexane is used as a soluble solvent to dissolve the carrier for separation, the complex compound can be crystallized by cooling the solution to 5° C. In addition, when a means of cooling the solvent is used as a means of changing the solution temperature, it becomes possible to facilitate the crystal growth by adding crystallization nuclei such as ODS particles (silica gel to the surface of which octadecyl group being bound) and glass beads.

Excision Process

In the method of separating a compound of the present invention, it is preferable to include a process of separating the complex compound of a compound to be the separation objective and the carrier for separation obtained in the crystallization process or the selection process into the compound and the carrier for separation.

Methods for separation into the compound and carrier for separation are not particularly limited so far as they are capable of cleaving the bond between the compound and the carrier for separation. For example, when a para-alkoxybenzyl bond is formed, it is possible to cleave the bond by the acid treatment.

(1) (ii) A Method of Performing Crystallization and/or Extraction after Dissolving the Carrier for Separation of the Present Invention in a Soluble Solvent and Sequentially Binding Amino Acids to the Carrier.

The method for separation of a compound of the present invention can be utilized as a synthesis method of a peptide using amino acids as the other compound.

The oligopeptide synthesis method of the present invention is a method including a dissolution process of dissolving the carrier for separation of the present invention in a soluble solvent to prepare a carrier solution; a binding process of obtaining the carrier for separation bound with an oligopeptide by binding an amino acid to the atomic group A of the carrier for separation, and sequentially binding other amino acids to the amino acid which has been bound to the carrier for separation; a crystallization process of crystallizing the carrier for separation while the oligopeptide is bound to the carrier for separation or a selection process of selectively extracting and/or selectively crystallizing the carrier for separation in a specific phase while the oligopeptide is bound to the carrier for separation; and an excision process of excising the oligopeptide from the carrier for separation bound with the oligopeptide after the crystallization process or the selection process.

Except that amino acids as other compounds are sequentially bound to the carrier for separation so as to make the carrier for separation to hold a peptide, the present method is common to the method (1) (i), in which crystallization and/or extraction are performed after the carrier for separation of the present invention is dissolved in a soluble solvent and the objective specific compound is bound to the carrier for separation, with respect of the dissolution process, impurity elimination process, and selection process (a means of changing the solution composition, a means of changing the solution temperature). Regarding the processes, see the above descriptions.

Binding Process

In the binding process, after binding an amino acid to the atomic group A which is the reaction site of the carrier for separation to obtain a complex compound of the amino acid and the carrier for separation, other amino acids are sequentially bound to the amino acid which has been bound to the atomic group A so as to obtain a complex compound of oligopeptide and the carrier for separation. That is, in the binding process, a plurality of amino acids are sequentially bound in a desired order with the atomic group A as a point of origin to obtain a complex compound of oligopeptide and the carrier for separation. The sequential binding may be performed in the same liquid phase containing the carrier for separation which has become a complex compound with the amino acid or oligopeptide, or in a different liquid phase once after the carrier for separation which has become a complex compound is solidified (crystallized) and separated.

Although the amino acids to be bound in this binding process are not particularly limited, protected amino acids used in the conventional solid phase reaction method such as Fmoc-amino acids and Cbz-amino acids can be used. Furthermore, the number of amino acids to be bound to the carrier for separation is not particularly limited, but preferably is in the range of 2 to 5.

Crystallization Process

In the crystallization process, the oligopeptide which has been bound to the carrier for separation in the previous binding process is crystallized while the oligopeptide is accompanied by the carrier for separation. In this crystallization process, any means may be used as far as the carrier for separation can be crystallized while the carrier for separation is bound with oligopeptide such as, for example, a means of changing the solution composition and/or a means of changing the solution temperature can be preferably used. In addition, when crystallization is performed after deprotecting the amino acid, it is possible to make the complex compound to crystallize easily by adding a weak acid such as formic acid to form the salt.

Excision Process

In the excision process, the oligopeptide is excised from a complex compound of oligopeptide with the carrier for separation obtained in the crystallization process or selection process. In the excision process, although a soluble reagent such as trifluoroacetic acid may be used, it is not easy to separate the acid from the excised oligopeptide, so that a solid phase reagent is preferably used. Solid phase reagents used in the excision process are not particularly limited so far as they are capable of excising oligopeptide from the complex compound, so that, for example, a solid acid, solid base and solid reducing agent can be used. Among them, as the solid acid reagent, for example, an acidic ion-exchange resin, acidic metal oxide, acidic combined metal oxide, metal sulfate, metal phosphate, crystalline metalosilicate, zeolite, silica alumina, etc. can be exemplified. More specifically, for example, a zeolite catalyst and montmorillonite can be exemplified.

(2) Method of Solidifying the Carrier for Separation of the Present Invention after Melting the Carrier for Separation Itself to a Liquid Phase and Binding a Specific Objective Compound Thereto in a Liquid Phase The separation method in which the carrier for separation itself of the present invention is melted to a liquid phase and reacted with a specific compound in the liquid phase includes a melting process of heating the carrier for separation of the present invention above the melting point to melt it to a liquid phase; a reaction process of reacting other compound with the reaction site A of the melted carrier for separation so as to bind the compound thereto; and a solidification process of solidifying the carrier for separation while the other compound is bound thereto.

Melting Process

The melting process in the present separation method is not particularly limited so far as it is a process of heating the carrier for separation above the melting point to melt the carrier itself to a liquid phase.

Reaction Process

The reaction process in the present separation method is a method of binding other compound to the reaction site A of the carrier for separation to obtain the complex compound of the carrier for separation and the other compound. The binding method in the reaction process is not particularly limited so far as it is a method of binding the other compound having a part capable of reacting with the reaction site A of the carrier for separation which has been fluidized in the previous process, so that, similar to the above-described first binding process, various chemical reactions in a liquid phase can be used. For example, a method of binding by forming the ester bond and amide bond can be exemplified. Also in the reaction process, for the purpose of maintaining the liquid phase, it is preferable to maintain the reaction temperature higher than the melting point of the carrier for separation.

Second Binding Process

The present separation process may include, after the above-described reaction process, a second binding process of further binding another compound to the other compound which has been bound to the reaction site A of the carrier for separation. The second binding process can be performed under similar conditions as those of the above-described second binding process.

Impurity Eliminating Process

Furthermore, in the present separation method, it is preferable to include an impurity eliminating process for eliminating impurities before performing the following solidification process similar to the above-described separation method.

Solidification Process

The solidification process in the present separation method is process in which after implementing the reaction process or furthermore a second binding process to the melted and fluidized carrier for separation to bind the other compound, etc., the carrier for separation is solidified to a solid phase while these compounds are bound to the carrier for separation. Although the method of solid phase transition in the solidification process is not particularly limited, it is preferable to perform the solid phase transition by a means of adding a poor solvent, in which the solubility of the complex compound of a compound to be the separation objective and the carrier for separation is low, to the complex compound because of easy operation.

Washing Process

Although, in the present separation method, separation of the objective specific compound is completed by a solid phase obtained in the above-described solidification process, a washing process may be arbitrarily implemented. The washing process is a process of washing the solid carrier for separation bound to the other compound with a poor solvent in which the solubility of this solid is low.

Impurity Elimination Process

In the present separation method, it is preferable to further include the impurity elimination process to eliminate impurities before performing the following extraction process similar to the above-described separation method.

Extraction Process

In the present separation method, it is preferable to include an extraction process of selectively extracting the complex compound of a compound to be the separation objective and the carrier for separation into a specific solvent after the abovementioned solidification process or washing process. Although the extraction process is not particularly limited, it is preferable to perform the extraction process by a means of adding a solvent capable of dissolving the complex compound of a compound to be the separation objective and the carrier for separation.

Excision Process

Furthermore, in the present separation method, it is preferable to include a process to separate the complex compound of a compound to be the separation objective and the carrier for separation into the compound and the carrier for separation after the above-described solidification process or extraction process, similar to the aforementioned separation method. When ending the operation with the solidification process, the excision process may be included after the solidification process, and when implementing procedures up to the extraction process, the excision process may be included after the extraction process.

(3) Method of Binding and Capturing the Objective Specific Compound (with the Carrier for Separation) after Dissolving the Carrier for Separation of the Present Invention in a Soluble Solvent and Subsequently Crystallizing (Solidifying) the Same The method for separation of a compound in which the carrier for separation of the present invention is dissolved in a soluble solvent and subsequently crystallized (solidified) before binding the objective compound to the carrier for separation includes: a dissolution process of dissolving the carrier for separation of the present invention in a soluble solvent to prepare a carrier solution; a crystallization process of crystallizing the carrier for separation; and a capturing process of capturing other compound by binding the other compound to the reaction site A of the crystallized carrier for separation.

Dissolution Process

The dissolution process in the present separation method can be performed by the same procedure as in the above-described dissolution process.

Crystallization Process

The crystallization process in the present separation method is a process of crystallizing (solidifying) the carrier for separation itself. Although the crystallization process in the present separation method is not particularly limited, so far as it is capable of crystallizing (solidifying) the carrier for separation, for example, a means of changing the composition of a solution in which the carrier for separation itself is dissolved and/or a means of changing the temperature of a solution in which the carrier for separation itself is dissolved can be preferably used.

Impurity Eliminating Process

Furthermore, in the present separation method, it is preferable to include an impurity eliminating process before implementing the following capturing process, similar to the above-described separation method.

Capturing Process

The capturing process in the present separation method is a process of binding a specific other compound having a part reactive to the reaction site A of the carrier for separation, which has been crystallized (solidified) in the previous process, to the reaction site A so as to obtain the complex compound of the carrier for separation and the other compound. The capturing process in the present separation method is not particularly limited, so far as it is a process (method) of binding the reaction site A and a specific other compound. For example, amide binding and ester binding can be exemplified.

Excision Process

Furthermore, in the present separation method, similar to the above-described separation method, it is preferable to include a process of separating the complex compound of a compound to be the separation objective and the carrier for separation obtained in the capturing process into the compound and the carrier for separation.

EXAMPLES

Next, the present invention is further described in detail with reference to Examples, but it is not to be construed as being limited thereto.

Example 1

Synthesis of Carrier for Separation

Hereinafter, a synthesis process chart of the carrier for separation of the present invention (compounds 2 and 5 in the FIGURE) is shown. Numerals in the figures represent the compound numbers.

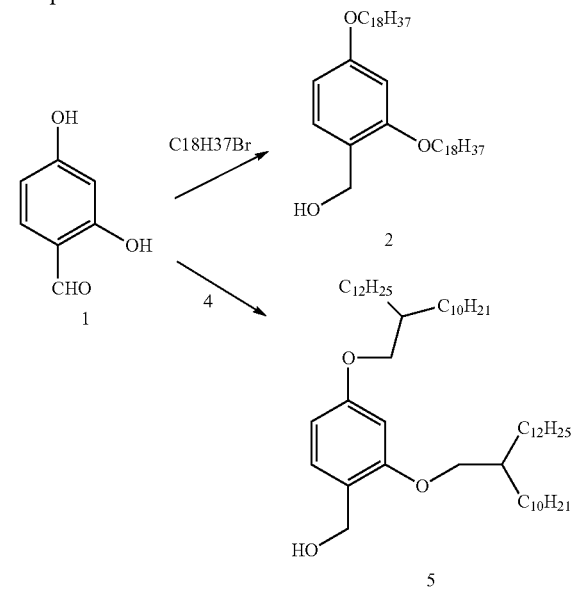

-continued

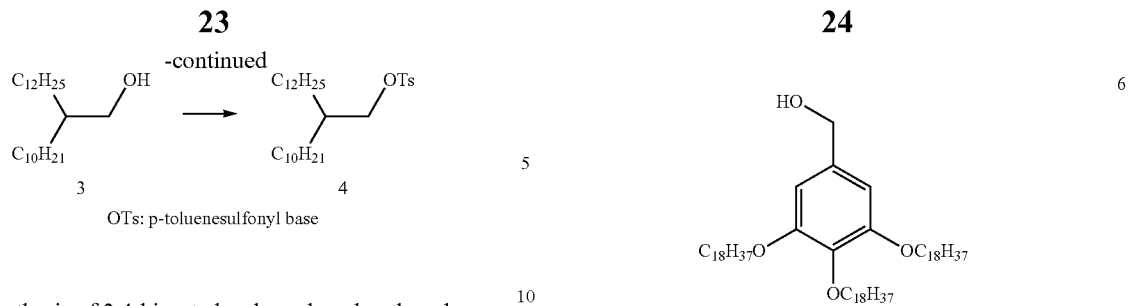

OTs: p-toluenesulfonyl base

Synthesis of 2,4-bisoctadecyloxyphenylmethanol (Compound 2)

After 2,4-dihydroxybenzaldehyde (compound 1) (1 g (0.0072 mol)) and octadecyl bromide (4.82 g (0.0145 mol)) were dissolved in dimethylformamide (DMF) (20 ml), potassium carbonate (5 g (0.0372 mol)) was added, and the resulting mixture was stirred under a nitrogen atmosphere at 100° C. for 6 hours. The reaction liquid thus obtained was extracted with hexane (3×100 ml), and subsequently this hexane solution was concentrated under vacuum. Methanol (MeOH) (200 ml) was added to the residue, and crystals thus produced were separated by filtration. After crystals thus obtained were dissolved in tetrahydrofuran (THF) (80 ml) and methanol (MeOH) (30 ml), sodium borohydride (0.7 g (0.0184 mol)) was added to the solution under stirring in an ice bath, and after stirring further for 1 hour, acetone (20 ml) was added to the mixture to terminate the reaction. Subsequently, after concentration under vacuum, water (50 ml) was added to the residue. The reaction solution thus obtained was extracted with hexane (3×100 ml), dried over anhydrous magnesium sulfate, and the solvent was distilled off under vacuum. Furthermore, methanol (MeOH) (200 ml) was added to the residue, and crystals thus produced were separated by filtration to obtain the objective compound 2 (2,4-bisoctadecyloxyphenylmetanol). The yield was 71%.

$^1$H-NMR (400 MHz, CDCl$_3$)

δ 7.12 (d, J=8.05, 1H), 6.45 (d, J=2.20, 1H), 6.41 (dd, J=8.05, 2.20, 1H), 4.60 (d, J=6.59, 2H), 3.97 (t, J=6.59, 2H), 3.93 (t, J=6.59, 2H), 1.86-1.69 (m, 4H), 1.52-1.15 (m, 60H), 0.93-0.83 (m, 6H)

$^{13}$C-NMR (75 MHz, CDCl$_3$)

δ 160.1, 158.2, 129.5, 121.7, 104.4, 99.8, 68.1, 68.0, 61.9, 31.9, 29.7, 29.6, 29.4, 29.3, 29.2, 26.1, 26.0, 22.7, 14.1

Evaluation of Solubility

The compound 2 (2,4-bisoctadecyloxyphenylmethanol) thus obtained was measured for solubility in hexane, cyclohexane, dichloromethane and tetrahydrofuran, respectively, when used as solvents at 25° C. Results are shown in Table 1.

TABLE 1

| | Solubility at 25° C. (mg/ml) | |
|---|---|---|
| Solvent | Example 1 (Compound 2) | Comparative Example 1 (Compound 6) |
| Hexane | 46.6 | 3 |
| Cyclohexane | 145 | 10 |
| Dichloromethane | 242 | 46 |
| Tetrahydrofuran | 370 | 184 |

Comparative Example 1

3,4,5-Tris-octadecyloxybenzylalcohol (compound 6) having the following chemical formula was measured for solubility in various solvents at 25° C. similar to as in Example 1. Results are shown in Table 1.

As shown in Table 1, compound 2 (2,4-bisoctadecyloxyphenylmethanol), one of the carriers for separation of the present invention is higher in solubility in commonly used solvents than the conventional compound 6 (3,4,5-tris-octadecyloxybenzylalcohol). Thus, the carrier for separation of the present invention can aim at improving the productivity.

Example 2

Synthesis of 2,4-bis-(2-decyl-tetradecyloxy)-phenylmethanol (compound 5)

2-Decyl-1-tetradecanol (compound 3) (9.7 g (0.0274 mol)) and pyridine (10.6 g (0.134 mol)) were dissolved in dichloromethane (100 ml), and tosyl chloride (15.5 g (0.0813 mol)) was added under stirring in an ice bath. After stirring for 3 hours at room temperature, ice water (20 ml) was added to the mixture to terminate the reaction. Hexane (200 ml) was added to the obtained reaction solution, and after washing the organic layer with 1 N HCl (3×100 ml), it was washed with a saturated sodium bicarbonate aqueous solution (3×100 ml), and further with a saturated NaCl solution three times. After drying over anhydrous magnesium sulfate, the solvent was distilled off under vacuum to obtain compound 4 (toluene-4-sulfonic acid 2-decyl-1-tetradecyl ester). The yield was 88%.

$^1$H-NMR (300 MHz, CDCl$_3$)

δ 7.78 (d, J=8.25, 2H), 7.33 (d, J=8.44, 2H), 3.91 (d, J=5.14, 2H), 2.44 (s, 3H), 1.65-1.51 (m, 1H), 1.38-1.02 (m, 40H), 0.90-0.78 (m, 6H)

After 2,4-dihydroxybenzaldehyde (293 mg (0.0021 mol)) and the above-obtained compound 4 (toluene-4-sulfonic acid 2-decyl-1-tetradecyl ester) (2.8 g (0.0055 mol)) were dissolved in dimethylformamide (DMF) (20 ml), potassium carbonate (1.5 g (0.0109 mol)) was added, and the resulting mixture was stirred under a nitrogen atmosphere at 100° C. for 16 hours. The reaction solution thus obtained was extracted with hexane (3×100 ml), and the obtained hexane solution was washed with a saturated NaCl aqueous solution (3×100 ml). Subsequently, after the hexane solution was dried over anhydrous magnesium sulfate and concentrated under vacuum, the residue was dissolved in tetrahydrofuran (THF) (100 ml) and methanol (MeOH) (40 ml), and sodium borohydride (240 mg (0.0063 mol)) was added to the solution under stirring in an ice bath. After the mixture was stirred further for 1 hour, acetone (20 ml) was added to terminate the reaction. After the concentration under vacuum, water (50 ml) was added, and the reaction solution was extracted with hexane (3×100 ml). Furthermore, after the combined hexane extracts were dried over anhydrous magnesium sulfate, the solvent was distilled off under vacuum, and the residue was purified by fractionation using silica gel chromatography (developing solution, hexane:ethyl acetate=20:1) to obtain the objective compound 5 (2,4-bis-(2-decyl-tetradecyloxy)-phenylmethanol. The yield was 70%.

$^1$H-NMR (300 MHz, CDCl$_3$)

δ 7.13 (d, J=8.07, 1H), 6.47-6.38 (m, 2H), 4.61 (d, J=6.42, 2H), 3.84 (dd, J=17.87, 6.42, 4H), 1.86-1.63 (m, 2H), 1.52-1.13 (m, 80H), 0.97-0.75 (m, 12H)

Example 3

Separation Method Using Carrier for Separation

Hereinafter, a process chart of the separation method using the carrier for separation (compound 2) obtained in Example 1 is shown. Numerals in the figures represent the compound numbers.

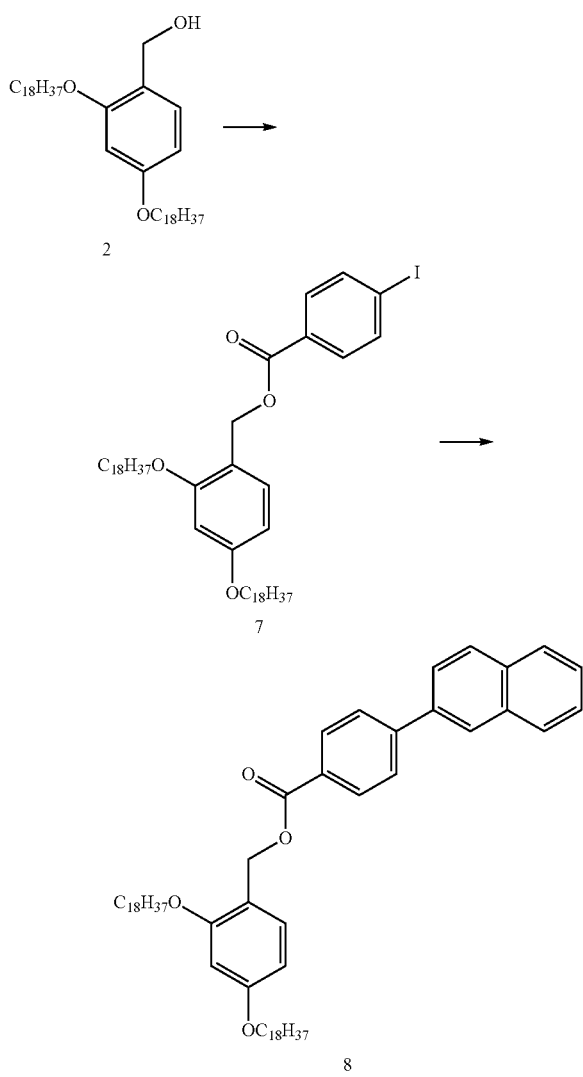

First Binding Process

Compound 2 (2,4-bis-octadecyloxyphenylmethanol), the carrier for separation of the present invention obtained in Example 1 (1 g (1.5502 mmol)), 4-iodobenzoic acid (0.77 g (3.1046 mmol)) and dimethylaminopyridine (100 mg (0.8195 mmol)) were dissolved in dichloromethane (50 ml), and diisopropylcarbodiimide (0.98 g (7.7778 mmol)) was further added, and the resulting mixture was stirred for 2 hours at room temperature. Subsequently, after distilling off the solvent under vacuum, methanol (MeOH) (200 ml) was added to the residue, and crystals were filtered to obtain 4-iodo-benzoic acid 2,4-bis-octadecyloxybenzyl ester (compound 7). The yield was 81%.

$^1$H-NMR (300 MHz, CDCl$_3$)

δ 7.78-7.71 (m, 4H), 7.27 (d, J=8.4, 1H), 6.48-6.42 (m, 2H), 5.32 (s, 2H), 4.02-3.87 (m, 4H), 1.86-1.65 (m, 4H) 1.51-1.13 (m, 64H), 0.95-0.80 (m, 6H)

Second Binding Process (Process of Coupling Other Compound to the Compound Bound to Carrier)

To the above-obtained compound 7 (4-iodo-benzoic acid 2,4-bis-octadecyoxybenzylester) (251 mg (0.2868 mmol)), palladium acetate (II) (3.2 mg (0.0151 mmol)) and tri-o-tolylphosphine (8.7 mg (0.0286 mmol)) was added dimethylformamide (DMF) (20 ml), and the mixture was stirred for 10 min. To the mixture thus obtained were added potassium phosphate (183 mg (0.8632 mmol)), 2-naphthaleneboronic acid (148 mg (0.8605 mmol)) and cyclohexane (20 ml), and the mixture was stirred at 80° C. for 20 hours. Upon cooling the reaction solution to room temperature, it became a two-layer solution. After recovering only the upper layer and concentrating it under vacuum, crystals formed were filtered by adding methanol (MeOH) (200 ml) to obtain compound 8 (4-naphthalen-2-yl-benzoic acid 2,4-bis-octadecyloxybenzylester) formed by coupling another compound to the compound bound to the carrier for separation. The yield was 80%.

$^1$H-NMR (300 MHz, CDCl$_3$)

δ 8.16 (d, J=8.3, 2H), 8.06 (s, 1H), 7.97-7.82 (m, 3H), 7.80-7.69 (m, 3H), 7.57-7.44 (m, 2H), 7.33 (d, J=8.8, 1H), 6.53-6.41 (m, 2H), 5.38 (s, 2H), 4.04-3.88 (m, 4H), 1.86-1.69 (m, 4H), 1.51-1.12 (m, 64H), 0.95-0.79 (m, 6H)

Separation Process

After the above-obtained compound 8 (4-naphthalen-2-yl-benzoic acid 2,4-bis-octadecyloxybenzylester) (100 mg) was dissolved in dichloromethane (30 ml), trifluoroacetic acid (0.3 ml) was added, and the mixture was stirred at room temperature for 30 min. Subsequently, after distilling off the solvent under vacuum and adding methanol (MeOH) (100 ml) to the residue, crystals were removed by filtration. The filtrate was distilled off under vacuum to obtain 4-naphthalen-2-yl-benzoic acid. The yield was 95%.

Evaluation of Separation Efficiency

By stirring the obtained compound 7 (4-iodo-benzoic acid 2,4-bis-octadecyloxybenzyl ester) in solvents listed in Table 2 and for the times shown in Table 2, separation of the compound from the carrier was performed to obtain the reaction rate. In this case, the reaction rate was calculated by assessing the disappearance of material by HPLC. Results are shown in Table 2.

TABLE 2

| | Reaction rate (%)* | |
|---|---|---|
| Excision reaction system | Example 3 (compound 7) | Comparative example 2 (compound 9) |
| 1% Trifluoroacetic acid/dichloromethane 30 min | 100 | 1< |
| 10% Trifluoroacetic acid/dichloromethane 120 min | 100 | 12 |
| 50% Trifluoroacetic acid/dichloromethane 120 min | 100 | 100 |

*Material consumption evaluated by HPLC measurement

Comparative Example 2

Regarding compound 9 (4-iodo-benzoic acid 3,4,5-tris-octadecyloxybenzyl ester) having the following formula 6, which was prepared by condensing 4-iodobenzoic acid to compound 6 (3,4,5-tris-octadecyloxybenzyl alcohol), the separation reaction rate was measured under various conditions similar to in Example 2. Results are shown in Table 2.

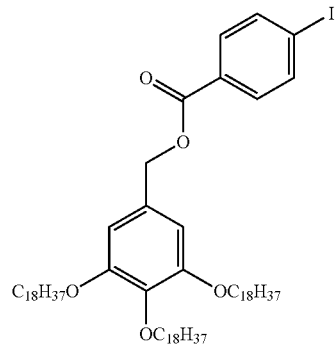

As shown in Table 2, compound 7 (4-iodo-benzoic acid 2,4-bis-octadecyloxybenzyl ester), one of complex compounds of the carrier for separation of the present invention and other compound, enables the separation process to be terminated under more moderate conditions and in a shorter time when compared with compound 9 (4-iodo-benzoic acid 3,4,5-tris-ocatadecyloxybenzyl ester), one of condensation products of the conventional carrier with the other compound. Therefore, the carrier for separation of the present invention can be applied even to acid-labile compound.

Example 4

The synthesis reaction was performed similar to Example 1, except for using 1-bromodocosane (5.64 g (0.0145 mol)) in place of octadecyloxybromide to obtain the objective compound (2,4-bis-docosanoxyphenyl methanol). The yield was 72%.

NMR measurement results are shown below.

$^1$H-NMR (400 MHz, CDCl$_3$)

δ 7.12 (d, J=8.29, 1H), 6.45 (d, J=2.20, 1H), 6.41 (dd, J=8.29, 2.20, 1H), 4.60 (d, J=6.59, 2H), 3.97 (t, J=6.59, 2H), 3.93 (t, J=6.59, 2H), 2.26 (t, J=6.59, 1H), 1.78 (m, 4H), 1.44 (m, 72H), 0.88 (t, J=6.83, 6H)

As a result of measuring the solubility of the obtained compound in tetrahydrofuran similar to Example 1, the solubility at 25° C. was 236 mg/ml.

Synthesis was performed similarly to in the first binding process of Example 3, except for using the above-described compound (1.17 g) in place of 2,4-bis-octadecyloxyphenyl methanol to obtain 4-iodo-benzoic acid 2,4-bis-docosanoxybenzyl ester. The yield was 80%.

$^1$H-NMR (300 MHz, CDCl$_3$)

δ 7.78-7.71 (m, 4H), 7.27 (d, J=8.4, 1H), 6.48-6.42 (m, 2H), 5.32 (s, 2H), 4.02-3.87 (m, 4H), 1.86-1.65 (m, 4H), 1.51-1.13 (m, 76H), 0.95-0.80 (m, 6H)

The above-obtained compound was evaluated for the separation efficiency, similar to Example 3, when it was stirred in dichloromethane containing 1% trifluoroacetic acid for 30 min. As a result, the reaction rate was 100%.

Example 5

Separation Method Using Carrier for Separation (Reaction Using Microwave)

Hereinafter, a process chart of the separation method using the carrier for separation (compound 2) obtained in Example 1 is shown. Numerals in the figures represent the compound numbers.

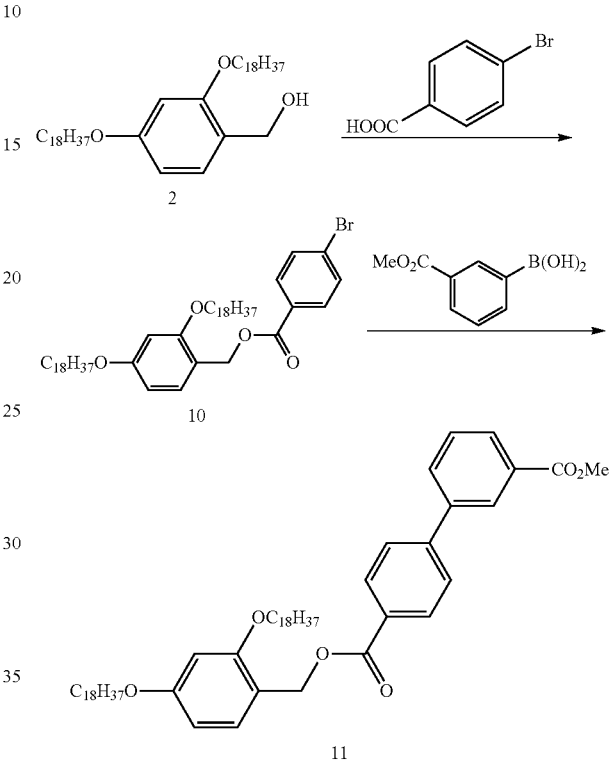

First Binding Process

Compound 2 (2,4-bis-octadecyloxyphenylmethanol), the carrier for separation of the present invention obtained in Example 1 (1 g (1.5502 mmol)), 4-bromobenzoic acid (0.62 g (3.1046 mmol)) and dimethylaminopyridine (100 mg (0.8195 mmol)) were dissolved in dichloromethane (50 ml), and diisopropylcarbodiimide (0.98 g (7.7778 mmol)) was further added, and the resulting mixture was stirred for 2 hours at room temperature. Subsequently, after distilling off the solvent under vacuum, methanol (MeOH) (200 ml) was added to the residue, and crystals were filtered to obtain compound 10 (4-bromo-benzoic acid 2,4-bis-octadecyloxybenzyl ester). The yield was 84%.

Second Binding Process (Process of Coupling Other Compound to the Compound Bound to Carrier)

To the above-obtained compound 10 (4-bromo-benzoic acid 2,4-bis-octadecyoxybenzyl ester) (24.8 mg (0.03 mmol)) and [1,1-bis-(diphenylphosphino)ferrocene]palladium (II) chloride (1.1 mg (0.0015 mmol)) was added dimethylformamide (DMF) (5 ml), and the mixture was stirred for 10 min. To the resulting mixture were added potassium phosphate (19.0 mg (0.09 mmol)), 3-methoxycarbonyl boronic acid (13.5 mg (0.075 mmol)) and cyclohexane (5 ml), and the mixture was irradiated with a microwave at 50 W for 10 min. After the irradiation, the mixture was cooled to room temperature to separate it to two phases. The upper layer was separated, and the solvent was distilled off under vacuum.

Methanol (30 ml) was added to the residue, and crystals were filtered to obtain compound 11 (biphenyl-3,4'-dicarboxylic acid 4'-(2,4-bis-octadecyloxy-benzyl)ester methyl ester. The yield was 99%.

Example 6

Separation Method Using Carrier for Separation (Flow Synthetic Reaction Using Microwave)

FIG. 1 shows a process chart of the separation method using the carrier for separation (compound 2) obtained in Example 1. Numerals in the figures represent compound numbers.

First Binding Process

Compound 2 (2,4-bis-octadecyloxyphenylmethanol), which is the carrier for separation of the present invention obtained in Example 1 (1 g (1.5502 mmol), 2-iodo-benzoic acid (0.77 g (3.1046 mmol)) and dimethylaminopyridine (100 mg (0.8195 mmol)) were dissolved in dichloromethane (50 ml), and diisopropylcarbodiimide (0.98 g (7.7778 mmol)) was further added, and the resulting mixture was stirred for 2 hours at room temperature. Subsequently, after distilling off the solvent under vacuum, methanol (MeOH) (200 ml) was added (to the residue), and crystals were filtered to obtain compound 12 (2-iodo-benzoic acid 2,4-bis-octadecyloxy-benzyl ester). The yield was 79%.

Second Binding Process (Process of Coupling Other Compound to the Compound Bound to Carrier)

The above-obtained compound 12 (2-iodo-benzoic acid 2,4-bis-octadecyoxybenzyl ester) (26.2 mg (0.03 mmol)) was dissolved in cyclohexane (4 ml). Separately, to dimethylformamide (4 ml) were added ethinylbenzene (30.6 mg (0.3 mmol)), dichloro-bis(triphenylphosphin)palladium (II) (4.2 mg (0.006 mmol)), triethylamine (30.3 mg (0.3 mmol)) and copper iodide (0.5 mg (0.003 mmol)), and the mixture was stirred. To the resulting mixture was added a cyclohexane solution of the above-obtained compound 12, and after air was replaced with nitrogen, flow synthesis was performed by the method shown in FIG. 1. In this case, the tube was made of 1 mm diameter Teflon (trademark), a tube of 170 cm being embedded in the microwave irradiation unit. While vigorously stirring the supply unit, the solution was supplied from the supply unit toward the recovery unit under microwave irradiation at 150 W and at flow rate of 3 ml/min. After running the entire solution, compound 13 (2-stilbenezoic acid 2,4-bis-octadecyloxybenzyl ester) was obtained from the upper layer of the recovery unit. The yield was 90%.

Example 7

Fmoc-Dipeptide Synthesis Using the Carrier for Separation of the Present Invention Dissolution of Carrier for Separation 2,4-Bis-dococyloxybenzyl alcohol represented by the following formula (2) (JITSIBO Co. Ltd, trade name: Hiver-Kb-OH) (hereinafter abbreviated as "Kb") was used as a carrier for separation, and 3800 mg (5 mmol) thereof was dissolved in dichloromethane (200 ml) to prepare a carrier solution.

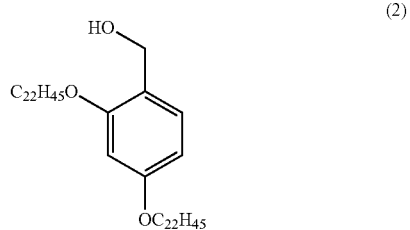

(2)

Binding of the First Amino Acid to Carrier for Separation

To the above-obtained carrier solution were added Fmoc-glycine (Gly)-OH (2300 mg (7.5 mmol)), dimethylaminopyridine (120 mg (1 mmol)) and diisopropylcarbodiimide (1.5 ml (10 mmol)) respectively, and the mixture was stirred for 30 min at room temperature. Completion of the reaction was confirmed by TLC (thin layer chromatography). After the reaction, acetonitrile (200 ml) was added to the reaction mixture, and the solvent was distilled off slowly under vacuum. Crystals thus obtained were filtered with a Kiriyama funnel to obtain the objective compound Kb-Gly-Fmoc. The yield was 92%. Furthermore, to a solution of this compound (3640 mg (3.5 mmol)) dissolved in dichloromethane (2.00 ml) was added DBU (1,8-diazabicyclo(5,4,0)undecene-7) (580 µl), and the mixture was stirred to react for 1 hour at room temperature. After the reaction was completed, formic acid (580 µl) and acetonitrile (200 ml) were added to the solution, respectively, and the solvent was distilled off slowly under vacuum. Crystals thus obtained were filtered with a Kiriyama funnel to obtain the objective compound Kb-Gly-H.

Binding of Second Amino Acid to Carrier for Separation

To a solution of the above-obtained Kb-Gly-H (2100 mg (2.6 mmol)) dissolved in dichloromethane (100 ml) were added Fmoc-alanine (Ala)-OH.H$_2$O (1000 mg (3 mmol)), HBTU (2-(1H-benzotriazol-1-yl)-1,1,3,3-tetramethyluroniumhexafluorophosphate) (1140 mg (3 mmol)), HOBt (1-hydroxybenzotriazole) (400 mg (3 mmol)), dimethylformamide (20 ml), and diisopropylethylamine (550 µl (3 mmol)), respectively, and the mixture was stirred to react for 1 hour at room temperature. After the reaction, acetonitrile (200 ml) was added, and the solvent was distilled off slowly under vacuum. Crystals thus obtained were filtered with a Kiriyama funnel to recover the objective compound Kb-Gly-Ala-Fmoc. The yield was 93%.

$^1$H-NMR (300 MHz, CDCl$_3$)

δ 7.76 (2H, d, J=7.2 Hz), 7.58 (2H, d, J=7.2 Hz), 7.40 (2H, t, J=7.2 Hz), 7.31 (2H, t, J=7.2 Hz), 7.18 (1H, d, J=7.9 Hz), 6.47-6.40 (3H, m), 5.32 (1H, br), 5.17 (2H, s), 4.51-4.16 (4H, m), 4.09-3.99 (2H, m), 3.98-3.87 (4H, m), 1.84-1.53 (7H, m), 1.47-1.19 (76H, m) 0.88 (6H, m)

Excision of Fmoc-Dipeptide Bound to the Carrier for Separation of the Present Invention by Solid Phase Reagent To a solution of the above-obtained Kb-Gly-Ala-Fmoc (1000 mg (0.90 mmol)) dissolved in dichloromethane (25 ml) was added a solid acid reagent (Sigma-Aldrich, Inc., trade name: Montmorillonite K10) (1000 mg), and the mixture was stirred to react at room temperature for 3.5 hours. Completion of the reaction was confirmed by TLC (thin layer chromatography). After the reaction, methanol (60 ml) was added, and the solvent was distilled off slowly under vacuum. The obtained crystalline Kb and the solid acid reagent were filtered with a Kiriyama funnel to recover the filtrate. The solvent of this filtrate was distilled off under vacuum, and the residue was dried under vacuum to recover the objective compound, Fmoc-Ala-Gly-OH. The yield was 69%.

As can be clearly seen from Example 7, the use of the carrier for separation represented by the above-described formula (2) enables Fmoc-dipeptide to be efficiently synthesized on the carrier for separation, and enables the carrier for separation bound with this Fmoc-dipeptide to be isolated. Furthermore, the treatment with a solid acid reagent enables Fmoc-dipeptide to be excised from the carrier for separation.

Example 8

Synthesis of Fmoc-Tripeptide Using the Carrier for Separation of the Present Invention
Dissolution of Carrier for Separation
Similar to Example 1, Kb was used as a carrier for separation, and 3800 mg (5 mmol) thereof was dissolved in cyclohexane (100 ml) to prepare a carrier solution.
Binding of First Amino Acid to Carrier for Separation
To the above-obtained carrier solution were added Fmoc-Leu-OH (2640 mg (7.5 mmol)), dimethylaminopyridine (120 mg (1 mmol)) and diisopropylcarbodiimide (1.5 ml (10 mmol)) in dimethylformamide (100 ml) respectively, and the mixture was stirred to react at 55° C. for 1 hour. Completion of the reaction was confirmed by TLC. After the reaction, the mixture was cooled to room temperature to become a two-layer solution, so that the upper layer solution containing Kb-Leu-Fmoc was recovered. To this upper layer solution was added dimethylformamide containing 1% DBU (70 ml) to form a two-layer solution, and the mixture was stirred to react at room temperature for 30 min. Completion of the reaction was confirmed by TLC. After the reaction, the upper layer solution containing Kb-Leu-H was recovered.
Binding of Second Amino Acid to Carrier for Separation
To the above-obtained upper layer solution were added Fmoc-Leu-OH (2640 mg (7.5 mmol)), HBTU (2850 mg (7.5 mmol)), HOBt (1000 mg (7.5 mmol)) and diisopropylethylamine (1375 µl (7.5 mmol)) in dimethylformamide (70 ml), respectively, and the mixture was stirred to react at 55° C. for 1 hour. Completion of the reaction was confirmed by TLC. After the reaction, the mixture was cooled to room temperature to become a two-layer solution, so that the upper layer solution containing Kb-Leu-Leu-Fmoc was recovered. To this upper layer solution was added dimethylformamide containing 1% DBU (70 ml) to form a two-layer solution, and the mixture was stirred to react at room temperature for 30 min. Completion of the reaction was confirmed by TLC. After the reaction, the upper layer solution containing Kb-Leu-Leu-H was recovered.
Binding of Third Amino Acid to Carrier for Separation
To the above-obtained upper layer solution were added Fmoc-Gly-OH (2230 mg (7.5 mmol)), HBTU (2850 mg (7.5 mmol)), HOBt (1000 mg (7.5 mmol)) and diisopropylethylamine (1375 µl (7.5 mmol)) in dimethylformamide (70 ml), respectively, and the mixture was stirred to react at 55° C. for 1 hour. Completion of the reaction was confirmed by TLC. After the reaction, when the reaction mixture was cooled to room temperature, it formed a two-layer solution, so that the upper layer solution containing Kb-Leu-Leu-Gly-Fmoc was recovered. After distilling off the solvent of this upper layer solution under vacuum slowly, methanol (300 ml) was added. Crystals thus obtained were filtered with a Kiriyama funnel to recover the objective compound Kb-Leu-Leu-Gly-Fmoc. The yield was 48%.
$^1$H-NMR (300 MHz, CDCl$_3$)
δ 7.74 (2H, d, J=7.5 Hz), 7.58 (2H, d, J=7.5 Hz), 7.38 (2H, dt, J=0.6, 7.5 Hz), 7.29 (2H, dt, J=0.9, 7.5 Hz), 7.14 (1H, d, J=8.7 Hz), 6.43-6.31 (3H, m), 6.28-6.21 (1H, m), 5.37 (1H, br), 5.15 (1H, d, J=11.7 Hz), 5.06 (1H, d, J=11.7 Hz), 4.62- 4.55 (1H, m), 4.49-3.34 (3H, m), 4.20 (1H, t, J=6.8 Hz), 3.95-3.81 (6H, m), 1.81-1.36 (10H, m), 1.34-1.14 (76H, m), 0.92-0.80 (18H, m)

As can be clearly seen from Example 8, the use of a carrier for separation represented by the above-described formula (2) enables Fmoc-tripeptide to be efficiently synthesized on the carrier for separation, and enables the carrier for separation bound to Fmoc-tripeptide to be separated. Especially, this Fmoc-tripeptide contains a Leu-Leu bond so as to be difficult to be synthesized by the solid phase reaction method. It is also possible to excise Fmoc-tripeptide from the carrier for separation by the treatment with a solid phase reagent.

Comparative Example 3

Excision of Fmoc-Dipeptide Bound to Another Carrier for Separation by Solid Phase Reagent
3,4,5-Tris-octadecyloxybenzyl alcohol represented by the following formula (3) (hereinafter abbreviated as "Ka") was used as a carrier for separation to recover Ka-Gly-Ala-Fmoc similarly as in Example 1. To a solution of Ka-Gly-Ala-Fmoc (1160 mg (0.92 mmol)) dissolved in dichloromethane (25 ml) was added a solid acid reagent, (Sigma-Aldrich, Inc., trade name: Montmorillonite K10) (1000 mg), and the mixture was stirred to react at room temperature for 3.5 hours. After the reaction, methanol (60 ml) was added, and the solvent was distilled off slowly under vacuum. The obtained crystals and the solid acid reagent were filtered with a Kiriyama funnel to recover the filtrate. Although the solvent of this filtrate was distilled off under vacuum and the residue was dried under vacuum, the objective compound Fmoc-Ala-Gly-OH could not be obtained.

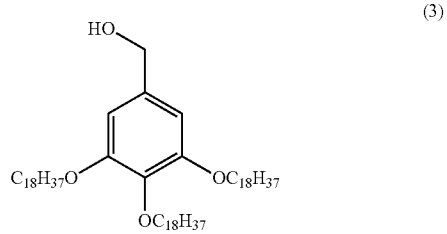

(3)

As can be clearly seen from comparative example 3, when the carrier for separation represented by the above-described formula (3) was used, Fmoc-dipeptide could not be obtained. This is apparently due to the bond between the carrier for separation Ka and dipeptide which is comparatively difficult to be cleaved, so that it was not cleaved by the solid acid reagent.

Comparative Example 4

Excision of Fmoc-Dipeptide Bound to Solid Phase Carrier by Solid Phase Reagent
Chloro-trityl(2-chloro)resin (Watanabe Chemical Industry) (hereinafter abbreviated as "CTC") (1.45 mmol/g) was used as a solid phase carrier, and CTC-Gly-Ala-Fmoc was synthesized by the solid phase reaction method. In addition, to a solution of CTC-Gly-Ala-Fmoc (580 mg, supported amount 0.84 mmol) dissolved in dichloromethane (25 ml) was added a solid acid reagent (Sigma-Aldrich, Inc., trade name: Montmorillonite K10) (1000 mg), and the mixture was stirred to react at room temperature for 3.5 hours. After the reaction, methanol (60 ml) was added, and the solvent was distilled off slowly under vacuum. The obtained crystals and the solid acid reagent were filtered with a Kiriyama funnel to recover the filtrate. Although the solvent of this filtrate was distilled off under vacuum and the residue was dried in vacuo, the objective compound Fmoc-Ala-Gly-OH could not be obtained.

As can be clearly seen from comparative example 4, when the solid phase carrier was used, Fmoc-dipeptide could not be obtained. This is apparently due to the insolubility of both the solid phase carrier and solid acid reagent in the reaction solution, so that they have no chance to interact each other, resulting in failure of bond cleavage.

Example 9

Tripeptide Synthesis by Solid Phase Reaction Using Fmoc-Dipeptide
Tripeptide Synthesis on Solid Phase Carrier Similar to comparative example 4, CTC-phenylalanine (Phe)-H was synthesized by the solid phase reaction method using CTC as a solid phase carrier. Furthermore, similar to Example 7, Fmoc-Ala-Gly-OH was synthesized. Then, to dichloromethane (2 ml) were added CTC-Phe-H (110 mg (0.145 mmol)), Fmoc-Ala-Gly-OH (160 mg (0.4 mmol)), HBTU (165 mg (0.4 mmol)), HOBt (60 mg (0.4 mmol)), dimethylformamide (1 ml) and diisopropylethylamine (75 µl (0.4 mmol)), respectively, and the mixture was stirred to react at room temperature for 2 hours. After the reaction, the solid phase was washed with dimethylformamide (3×2 ml), methanol (3×2 ml) and dichloromethane (3×2 ml), respectively. Subsequently, to the above solid phase was added the previously prepared Fmoc deprotection solution (dimethylformamide:piperidine:DBU=96:2:2) (2 ml), and the mixture was stirred to react at room temperature for 1 hour to obtain CTC-Phe-Gly-Ala-H.
Excision of Tripeptide Bound to Solid Phase Carrier The above-obtained CTC-Phe-Gly-Ala-H was washed with dimethylformamide (3×2 ml), methanol (3×2 ml), and dichloromethane (3×2 ml), respectively. Subsequently, the previously prepared excision fluid (dichloromethane containing 1% trichloroacetic acid) (20 ml) was added, and the resulting mixture was stirred to react for 30 minutes at room temperature. After the reaction, the solution was filtered through a Kiriyama funnel to recover the filtrate. The solvent of this filtrate was distilled off under vacuum, and the residue was dried in vacuo to obtain the objective compound H-Ala-Gly-Phe-OH. As a result of high-performance liquid chromatography, purity was 94%.

As can be clearly seen from Example 9, the use of Fmoc-dipeptide synthesized using a carrier for separation represented by the above-described formula (2) as a material of the solid phase reaction method enables tripeptide to be synthesized in a fewer number of processes, rapidly, and in high purity.

Comparative Example 5

Tripeptide Synthesis by Solid Phase Reaction Method
Tripeptide Synthesis on Solid Phase Carrier Similar to comparative example 4, CTC-Phe-H was synthesized by the solid phase reaction method using CTC as a solid phase carrier. Then, to dichloromethane (2 ml) were added CTC-Phe-H (110 mg (0.145 mmol)), Fmoc-Gly-OH (120 mg (0.4 mmol)), HBTU (165 mg (0.4 mmol)), HOBt (60 mg (0.4 mmol)), dimethylformamide (1 ml) and diisopropylethylamine (75 µl (0.4 mmol)), respectively, and the mixture was stirred to react at room temperature for 2 hours. After the reaction, the solid phase was washed with dimethylformamide (3×2 ml), methanol (3×2 ml) and dichloromethane (3×2 ml), respectively. Subsequently, to the solid phase was added the previously prepared Fmoc deprotection solution (dimethylformamide:piperidine:DBU=96:2:2) (2 ml), and the mixture was stirred to react at room temperature for 1 hour to obtain CTC-Phe-Gly-H. This CTC-Phe-Gly-H was dissolved in dichloromethane (2 ml), and Fmoc-Ala-OH.H$_2$O (130 mg (0.4 mmol)), HBTU (165 mg (0.4 mmol)), HOBt (60 mg (0.4 mmol)), dimethylformamide (1 ml) and diisopropylethylamine (75 µl (0.4 mmol)) were added, respectively, and the mixture was stirred to react at room temperature for 2 hours. After the reaction, the solid phase was washed with dimethylformamide (3×2 ml), methanol (3×2 ml), and dichloromethane (3×2 ml), respectively. Subsequently, to the solid phase was added the previously prepared Fmoc deprotection solution (dimethylformamide:piperidine:DBU=96:2:2) (2 ml), and the mixture was stirred to react at room temperature for 1 hour to obtain CTC-Phe-Gly-Ala-H.
Excision of Tripeptide Bound to Solid Phase Carrier The above-obtained CTC-Phe-Gly-Ala-H was washed with dimethylformamide (3×2 ml), methanol (3×2 ml), and dichloromethane (3×2 ml), respectively. Subsequently, the previously prepared excision solution (dichloromethane containing 1% trichloroacetic acid) (20 ml) was added, and the resulting mixture was stirred to react for 30 minutes at room temperature. After the reaction, the solution was filtered through a Kiriyama funnel to recover the filtrate. The solvent of this filtrate was distilled off under vacuum, and the residue was dried in vacuo to obtain the objective compound H-Ala-Gly-Phe-OH. As a result of high-performance liquid chromatography, purity was 88%.

As can be clearly seen from comparative example 5, the tripeptide could be synthesized as usual by a conventional solid phase reaction method, but purity of the product was lower compared with Example 9. This is probably due to, for example, a partial failure of the reaction of CTC-Phe-H with Fmoc-Gly-OH and instead due to the reaction of CTC-Phe-H with the subsequently added Fmoc-Ala-OH.H$_2$O, resulting in the synthesis of a dipeptide, H-Ala-Phe-OH, or due to a partial failure of the reaction of CTC-Phe-Gly-H with Fmoc-Ala-OH.H$_2$O, resulting in the synthesis of a dipeptide, H-Gly-Phe-OH.

INDUSTRIAL APPLICABILITY

The carrier for separation and the method of separating a compound according to the present invention enable the research and development of drugs, etc. by compound library synthesis or the like to be promoted, so as to be able to eventually contribute to technical innovation in the biochemical industry and chemical industry. Furthermore, the present invention is able to become an innovative technique in the separation and purification of biochemical substances, the search for drug candidate substances, and the constitution of novel chemical synthetic reaction methods and continuous synthesis method of peptides, etc.

The invention claimed is:
1. A method for synthesizing an oligopeptide comprising:
a dissolution process for dissolving a carrier for separation in a soluble solvent to prepare a carrier solution; wherein the carrier for separation is a compound having the following chemical formula (1),

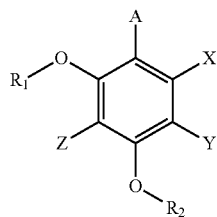

(1)

wherein the reaction site A is an atomic group having hydroxyl group, thiol group, amino group or carboxyl group which binds to an amino acid;
X, Y and Z are hydrogen; and
$R_1$ and $R_2$ are groups, which may be identical or different, containing at least 1 of a hydrocarbon group having a carbon number in the range of 14 to 60 which may have a substituent, and an acyl group having a carbon number in the range of 14 to 60 which may have a substituent;
a binding process for obtaining the carrier for separation bound with an oligopeptide by binding an amino acid to the reaction site A of the carrier for separation and sequentially binding other amino acids to the amino acid which has been bound to the carrier for separation;
a crystallization process for crystallizing the carrier for separation while the oligopeptide is bound to the carrier, or a selection process for selectively extracting and/or selectively crystallizing the carrier for separation into a specific phase while the oligopeptide is bound to the carrier; and
after the crystallization process or the selection process, an excision process for excising the oligopeptide from the carrier for separation to which the oligopeptide has been bound.

2. The method for synthesizing an oligopeptide according to claim 1, wherein the $R_1$ and $R_2$ of the carrier of separation are groups, which may be identical or different, containing at least 1 of a hydrocarbon group having a carbon number in the range of 14 to 30 which may have a substituent, and an acyl group having a carbon number in the range of 14 to 30 which may have a substituent.

3. The method for synthesizing an oligopeptide according to claim 1, wherein the crystallization process or the selection process is performed by a means of changing the composition of a solution in which the carrier for separation dissolves and/or a means of changing the temperature of a solution in which the carrier for separation dissolves.

4. The method for synthesizing oligopeptide according to claim 1, wherein the excision process is performed by adding a solid phase reagent to a solution in which the carrier for separation is dissolved.

5. The method for synthesizing oligopeptide according to claim 4, wherein the solid phase reagent is a solid acid reagent.

* * * * *